United States Patent

Deason et al.

[11] Patent Number: 4,923,891
[45] Date of Patent: * May 8, 1990

[54] LEUKOTRIENE LTD₄ AND LTB₄ ANTAGONISTS

[75] Inventors: James R. Deason, Wilmette; Michael A. Stealey, Libertyville; Richard M. Weier, Lake Bluff, all of Ill.

[73] Assignee: G. D. Searle & Co., Chicago, Ill.

[*] Notice: The portion of the term of this patent subsequent to Feb. 28, 2006 has been disclaimed.

[21] Appl. No.: 241,265

[22] Filed: Sep. 9, 1988

Related U.S. Application Data

[63] Continuation-in-part of Ser. No. 100,685, Sep. 24, 1987, Pat. No. 4,808,729.

[51] Int. Cl.⁵ .......................................... A61K 31/335
[52] U.S. Cl. ................................. 514/433; 514/436; 514/452; 549/30; 549/39; 549/454
[58] Field of Search .................... 514/97, 98, 101, 433, 514/436, 452; 549/30, 39, 454

[56] References Cited

U.S. PATENT DOCUMENTS 4,710,505 12/1987 Robin et al. .................. 549/454

FOREIGN PATENT DOCUMENTS 1448340 6/1966 France ................... 514/97
0004493 10/1966 France ................... 549/454
1445013 10/1966 France ................... 514/97

OTHER PUBLICATIONS

McCarthy, et al., J. Med. Chem., 28:1145–1147, (1985).

Primary Examiner—Richard A. Schwartz
Assistant Examiner—Zinna Northington-Davis
Attorney, Agent, or Firm—Mary Jo Kanady; Paul D. Matukaitis

[57] ABSTRACT

This invention encompasses compounds of Formula I

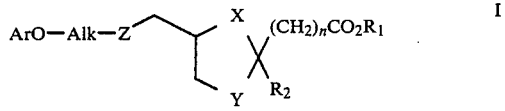

and the pharmaceutically acceptable salts and geometrical and optical isomers thereof wherein:

X, Y, and Z are each independently O or S with S optionally oxidized to S=O;

Alk is straight or branched chain alkylene or hydroxyalkylene containing 1–6 carbon atoms;

$R_1$ is hydrogen or lower alkyl;

n is 0 to 5;

$R_2$ is hydrogen, lower alkyl, cycloalkyl, —$(CH_2)_n$—$CO_2R_1$, phenyl, phenyl substituted with halo, lower alkyl or lower alkoxy; and Ar is 5,6,7,8-tetrahydro-1-naphthalenyl, phenyl, or phenyl substituted with lower alkyl, hydroxy, lower alkoxy, or lower alkanoyl.

This invention is in the field of pharmaceutical agents which act as leukotriene D₄ (LTD₄) antagonists and includes embodiments which act as leukotriene B₄ (LTD₄) antagonists.

40 Claims, No Drawings

LEUKOTRIENE LTD4 AND LTB4 ANTAGONISTS

This is a continuation-in-part of application Ser. No. 07/100,685 filed Sept. 24, 1987 now U.S. Pat. No. 4,808,729.

BACKGROUND OF THE INVENTION

1. Field of the Invention

This invention is in the field of pharmaceutical agents which act as leukotriene $D_4$ ($LTD_4$) antagonists and includes embodiments which act as leukotriene $B_4$ ($LTD_4$) antagonists.

2. Prior Art

The prior art generally describes $LTD_4$ antagonists as anti allergy compounds and $LTB_4$ antagonists as anti inflammatory agents.

Leukotriene $D_4$ and $C_4$ ($LTD_4/LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil stimulation and is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases. Dioxolane-2-carboxylic acids of the formula

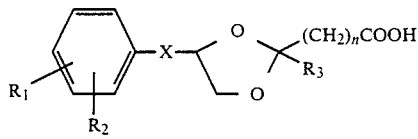

where
- $R_1$ and $R_2$ are the same or different H, halogen, alkyl, or alkoxy;
- $R_3$ is H, alkyl, aryl or alkyl optionally substituted by halogen, lower alkyl, or lower alkoxy;
- X is $-CH_2-$, $-OCH_2-$ where the O is joined to the phenyl;
- n is 0–3, are taught as sedatives or choleretic agents in French Patent No. 1,445,013.

SUMMARY OF THE INVENTION

This invention encompasses novel compounds of the hereinafter described Formula I, pharmaceutical formulations containing such compounds, and the use of these formulations as anti-allergy agents and anti-inflammatory agents. The invention encompasses compounds of Formula II which are $LTD_4$ antagonists, pharmaceutical compositions thereof, and the use of such formulations as anti-allergy agents. The invention also encompasses compounds of Formula III which are $LTB_4$ antagonists, pharmaceutical formulations thereof, and the use of such formulations in treating anti inflammatory diseases.

DETAILED DESCRIPTION

This invention encompasses compounds of Formula I

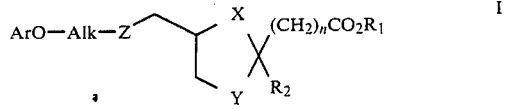

and the pharmaceutically acceptable salts and geometrical and optical isomers thereof wherein:

- X, Y, and Z are each independently O or S with S optionally oxidized to S=O;
- Alk is straight or branched chain alkylene or hydroxyalkylene containing 1–6 carbon atoms;
- $R_1$ is hydrogen or lower alkyl;
- n is 0 to 5;
- $R_2$ is hydrogen, lower alkyl, cycloalkyl, $-(CH_2)_n-CO_2R_1$, phenyl, phenyl substituted with halo, lower alkyl or lower alkoxy; and
- Ar is 5,6,7,8-tetrahydro-1-naphthalenyl, phenyl, or phenyl substituted with lower alkyl, hydroxy, lower alkoxy, or lower alkanoyl.

A preferred embodiment is a compound of formula II

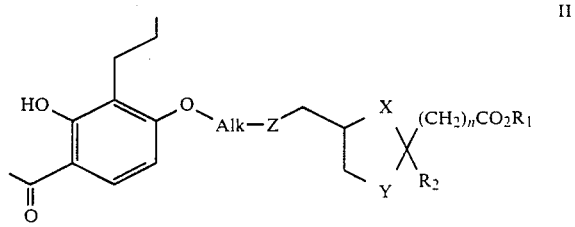

where Alk, Z, X, Y, $R_2$, n, and $R_1$ are as defined before. These compounds are characterized as having $LTD_4$ antagonist activity. A most preferred embodiment is compounds of formula II wherein $R_2$ is lower alkyl and $R_1$ is hydrogen as represented by Examples 61, 84 and 128(c). These compounds are particularly preferred because of their potency and oral availability.

This invention also encompasses compounds of formula III

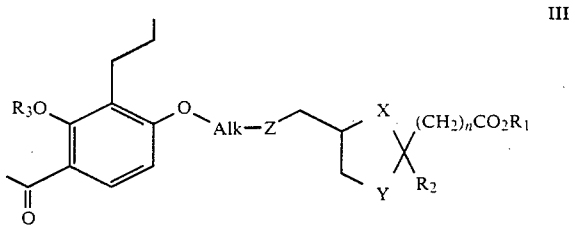

where $R_3$ is lower alkyl and Alk, Z, X, Y, n, $R_1$, and $R_2$ are as previously defined. These compounds are $LTB_4$ antagonists and are useful as anti-inflammatory agents.

The dioxolane compounds may be prepared as shown in Scheme A. The starting compound

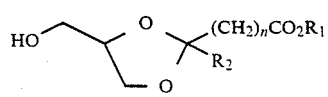

may be prepared using the procedure described in C. R. ACAD. SC. PARIS, t.271 (July 20, 1970) p 218–220 or R. Bohm, PHARMAZIE, 36:329 (1981).

SCHEME A

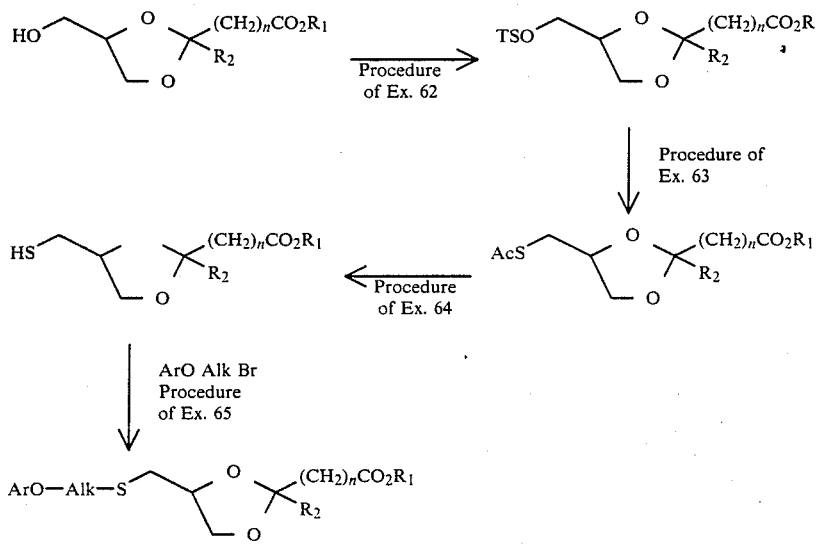

ArO, Alk, $R_1$, $R_2$ and n are defined as in Formula I.

The term "lower alkyl" means straight or branched chain alkyl having 1 to 6 carbon atoms such as methyl, ethyl, propyl, butyl, pentyl, hexyl and the branched chain isomers thereof.

The term "lower alkoxy" means straight or branched chain alkoxy having 1 to 6 carbon atoms such as methoxy, ethoxy, propoxy, butoxy, pentoxy, hexoxy and the branched chain isomers thereof.

The term "lower alkanoyl" means straight or branched chain alkanoyl having 2 to 6 carbon atoms such as acetyl, propanoyl, butanoyl, pentanoyl, hexanoyl and the branched chain isomers thereof.

The term "halo" means fluoro, cloro, bromo, or iodo.

The term "pharmaceutically acceptable salts" means non toxic salts of the acids of the compounds of this invention where the cation is sodium, potassium, lithium, calcium, magnesium, zinc, ferrous, aluminum, ammonium, tetraalkylammonium, and the like.

Compounds of this invention are generally prepared according to the following scheme:

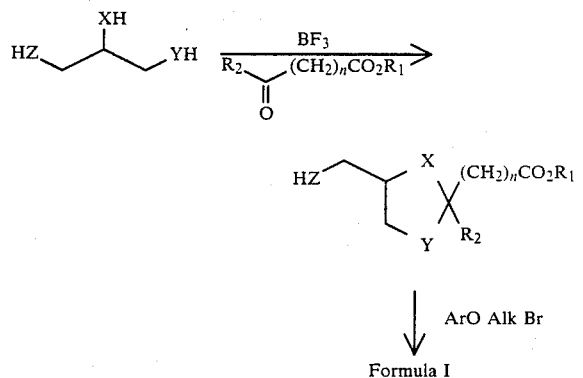

Formula I where Ar, X, Y, Z, n, Alk, $R_1$ and $R_2$ are as earlier defined. Optical isomers are resolved into enantiomers by conventional techniques.

The hereinafter set out examples further illustrate methods for preparing compounds of this invention.

The $LTD_4$ antagonist utility compounds are illustrated by activity in one or more of the following tests.

$LTD_4$ Antagonism in Guinea Pig Ileum

Fresh segments of guinea pig ileum were suspended in 2 ml. tissue baths containing oxygenated modified Tyrodes solution. After an equilibration period, an agonist dose-response curve was generated by exposing each tissue to 4 different $LTD_4$ doses and measuring the ensuing contractile heights. The ileum segments were washed and rested between exposures to agonist. Following this, the tissues were incubated with a single concentration of test compound and the agonist dose response procedure was repeated. The dose ratio is a measure of the antagonist's ability to shift the agonist dose response curve to the right. It is derived as the concentration of agonist necessary to reach a given response level in the presence (A') versus the absence (A) of antagonist. For example, if the test concentration of compound had no effect on the agonist induced response (A'=A) the dose ratio would approximate 1. Dose ratios increase if the compound inhibits the agonist induced response. One dose ratio value is determined for each strip of ileum used to test antagonist. If the dose ratios increase as a function of increasing antagonist concentration, these data may be evaluated by Schild analysis to determine whether the inhibition is competitive and if so, what the $pA_2$ value is for that compound. Schild analysis examines the linearity of the function described by the dose-ratios written as log [(A'/A)−1] versus antagonist concentration. If the linearity is confined and the slope approximates 1, inhibition is considered to be competitive. The $pA_2$ is the negative log of the antagonist concentration required to produce a dose-ratio of 2. This value is considered to be a measure of the affinity of the competitive antagonist.

In Vivo Assay

The compounds are tested in vivo as follows. Adult male fasted Hartly guinea pigs weighing 300–350 g are pretreated with pyrilamine and indomethacin to block the bronchoconstricture effects of endogenous histamine and the synthesis of thromboxane A2 respectively.

Compounds of the invention are administered IV or IG at approximate times prior to the IV administration of 2000 units of $LTD_4$. Intratracheal pressure is monitored prior to and subsequent to $LTD_4$ in animals anesthetized with pentobarbital and attached to a rodent respirator. Compounds which antagonize the direct component of $LTD_4$ action on respiratory smooth muscle inhibit intratracheal insufflation pressure increases (P<or =0.05) caused by $LTD_4$. FPL 55712 is used as a control.

Leukotriene Receptor Binding Assay (12c01)

The in vitro $LTD_4$ receptor binding assay is carried out as follows:

Specific binding of titrated $LTD_4$ to a fixed number of guinea pig lung receptors, isolated from guinea pig lung membrane, is measured in the presence and absence of test compound. The initial screening dose ($1 \times 10^{-5}$ M is considered active if the specific binding of the $LTD_4$ is reduced by 45% or more. Active compounds are tested in a dose-response manner to determine $IC_{50}$ values.

$LTB_4$ activity of compounds of this invention is indicated by the following tests.

Preparation of Human Neutrophils

Neutrophils were purified from venous blood of normal human donors using standard techniques of dextran sedimentation, centrifugation on Histopaque sterile solution (Sigma) and hypotonic lysis of erythrocytes (Boyum, A., *Isolation of Leukocytes From Human Blood: Further Observations.* Scand J. Lab. Clin. Invest. 21 (Suppl. 97): 31, 1968). The purity of isolated neutrophils was $\geq 95\%$.

$LTB_4$ Receptor Binding Assay

Neutrophils ($4-6 \times 10^6$) in 1 ml Hanks' balanced salt solution containing 10 mM HEPES buffer (HBSS), pH 7.4 and 30 mM nordihydroguaiaretic acid were incubated with 0.6 nano M ($^3$H) $LTB_4$ in the presence or absence of test compounds. The incubation was carried out at 0° C. for 45 minutes and terminated by adding 5 ml of ice cold HBSS followed by rapid filtration of incubation mixture under vacuum through GF/C glass fiber filters. The filters were further washed with 10 ml HBSS and radioactivity was determined. Specific binding was defined as the difference between total binding and nonspecific binding which was not displaced by $10^{-7}$ M unlabeled $LTB_4$. All data refer to specific binding.

Human Neutrophil Degranulation Assay

Neutrophil degranulation was determined by measuring the release of myeloperoxidase activity into the incubation medium. Neutrophils ($3 \times 10^6$) in 1 ml HBSS solution were preincubated with cytochalasin B(5$\mu$g) at 37° C. for 5 minutes, followed by preincubation with test compounds for 7 minutes. Neutrophils were then incubated for 2 to 20 minutes with either $LTB_4$ ($5 \times 10^{-8}$ M) or the chemotactic peptide f-met-leu phe ($5 \times 10^{-6}$ M) to induce degranulation. Following incubation, samples were centrifuged and myeloperoxidase was extracted from the cell pellets by sonication in phosphate buffer containing 0.4% Triton X-100. Triton X 100 was also added to the supernatants to a concentration of 0.4%. The supernatants and the pellet - extracts were then assayed spectrophotometrically for myeloperoxidase activity by determining the rate of decomposition of $H_2O_2$ with o-dianisidine as hydrogen donor as described by Renlund, et al. (Renlund, D. G., MacFarlane, J. L., Christensen, R. D., Lynch, R. E., and Rothstein, G., *A Quantitative And Sensitive Method for Measurement of Myeloperoxidase,* Clinical Research 28:75A, 1980). Myeloperoxidase activity released into the supernatant was expressed as the percent of the average total activity (pellet plus supernatant).

Guinea Pig $LTB_4$ Induced Dermal Chemotaxis

Test compound was administered intravenously or intragastrically at various times prior to the injection of leukotriene $B_4$ ($LTB_4$). $LTB_4$ was diluted in phosphate buffered saline (PBS) and 35 ng in 0.2 ml were injected intradermally into the shaven backs of anesthetized guinea pigs. PBS was injected as control. Four hours later, animals were sacrificed, skins removed and stored frozen ($-70°$ C). Injection sites were removed with a skin punch and mechanically homogenized (Polytron, Brinkmann Instruments). Myeloperoxidase (MPO), a marker enzyme for neutrophils, was extracted by 0.5% hexadecyltrimethylammonium bromide in 50 mM potassium phosphate buffer (pH 6.0), using sonication and freeze thaw procedures. After centrifugation (40,000 x g, 30 minutes), enzyme activities in the supernatants were assayed spectrophotometrically ($A_{460}$) by measuring the decomposition of hydrogen peroxide with ortho dianisidine after 15 minutes. MPO activity was found to be proportional to the number of neutrophils. In guinea pigs the level of MPO activity increased with the amount of $LTB_4$ injected.

Modified Boyden Chamber Chemotaxis

Human neutrophils were isolated from citrated peripheral blood sedimented in 5% dextran, followed by centrifugation on Histopaque sterile solution (Sigma) and hypotonic lysis of erythrocytes. A final cell suspension of $3-4 \times 10^6$ neutrophils/ml of HEPES buffered Hanks' balanced salt solution (HBSS, pH 7.3) was added to the upper well (0.8 ml) of a modified Boyden chamber (blind well). The lower well (0.2 ml), separated by a polycarbonate membrane (Nuleopore Corp.), contained HBSS or $3 \times 10^{-8}$ M $LTB_4$ in the presence or absence of test compound. Following a 90 minute incubation at 37° C. in 5% $CO_2$-95% air, cells from the lower well were lysed and nuclei counted in a Model S Plus-IV Coulter counter. Percent inhibition was calculated from cell counts corrected for random migration by subtracting the mean of the HBSS control.

Table 1 illustrates the $LTD_4$ and $LTB_4$ activity of representative compounds of this invention.

TABLE I

| Example | Receptor Binding Assay ($IC_{50}$) | Guinea Pig Ileum Assay ($pA_2$) | In Vivo Bronchoconstriction Assay (% Inhibition at 5mpk. IV) |
|---|---|---|---|
| $LTD_4$ ANTAGONISM ||||
| 35 | 0.591 $\mu$M | 8.05 | 93 |
| 38 | 9.37 $\mu$M | 7.84 | 87.2 |
| 61 | 5.02 $\mu$M | 8.02 | 95.6 |
| 50 | 9.47 $\mu$M | 7.84 | 91.2 |
| 84 | 7.10 $\mu$M | 7.77 | 85.1 |
| 3 | 3.56 $\mu$M | 7.67 | 96.9 |
| 70 | 6.24 $\mu$M | 7.57 | 59.2 |
| $LTB_4$ ANTAGONISM ||||
| 81 | 0.06 $\mu$M | | |

The compounds can be administered in such oral dosage forms as tablets, capsules, softgels, pills, powders, granules, elixirs, or syrups. The compounds may also be administered intravascularly, intraperitoneally, subcutaneously, or intramuscularly, using forms known to the pharmaceutical art. In general, the preferred form of administration is oral. For the orally administered pharmaceutical compositions and methods of the present invention the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, the active drug components may be combined with any oral non toxic pharmaceutically acceptable inert carrier such as lactose, starch, sucrose, cellulose, magnesium stearate, dicalcium phosphate, combinations thereof. For oral administration in liquid forms, such as in softgels, elixirs, syrups, drops and the like, the active drug components may be combined with any oral non toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methyl-cellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components may be combined with a suitable carrier such as water, saline, aqueous dextrose, and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Moreover, the compounds or their salts may be used in a suitable hydrated form.

Topical formulations of salves and ointments are useful in treating conditions such as psoriasis.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention are ordinarily in the range of about 1 to 50 mg/kg are generally suitable.

The accompanying examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

DESCRIPTION OF THE PREFERRED EMBODIMENTS

EXAMPLE 1

Diethyl 4-(mercaptomethyl)-1,3-oxathiolane 2,2-dipropanoate

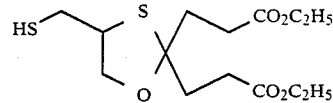

Diethyl 4-oxo pimelate (37 g, 0.16 mol) and 2,3-dimercapto-pb 1-propanol (20 g, 0.16 mol) were dissolved in methylene chloride (600 ml). Distilled boron trifluoride etherate (5 ml) was added and the reaction was stirred for three days at room temperature under a nitrogen atmosphere.

The reaction was quenched by adding 5% aqueous potassium bicarbonate solution (200 ml). The layers were separated and the organic phase was washed with water and dried over magnesium sulfate. The drying agent was filtered and the filtrate concentrated on the rotary evaporator. The residual oil was chromatographed on silica gel using 3% ethyl acetate/toluene as eluent to give 27.5 g (51%) of the above titled compound as an oil.

Analysis calculated for $C_{14}H_{24}O_5S_2$: Calc.: C, 49.99; H, 7.19; S, 19.03. Found: C, 49.92; H, 7.23; S, 19.11.

EXAMPLE 2

Diethyl 4-[[[3 (4-acetyl-3-hydroxy-2-propylphenoxy)propyl]thio]methyl]-1,3 oxathiolane-2,2-dipropanoate

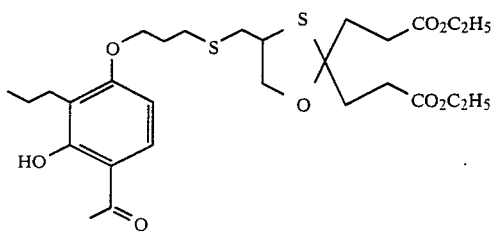

30(2-n-Propyl-3-hydroxy-4 acetylphenoxy)-1-bromopropane (2.0 g, 0.006 mol), prepared by the method described in U.S. Pat. No. 4,565,882, Example 14, incorporated herein by reference, was dissolved in methyl ethyl ketone (20 ml). To this solution was added the thiol of Example 1 (2.0 g, 0.006 mol) and anhydrous potassium carbonate (2.5 g) and the reaction mixture was refluxed with stirring under a nitrogen atmosphere for 24 hrs. The reaction was cooled to room temperature, filtered and the filtrate concentrated on the rotary evaporator. The residue was chromatographed on silica gel using 25% ethyl acetate/hexane as eluent to give 3.3 g (95%) of the title compound as an oil.

Analysis calculated for $C_{28}H_{42}O_8S_2$: Calc.: C, 58.73; H, 7.41; S, 11.21. Found: C, 58.55; H, 7.40; S, 11.51.

EXAMPLE 3

4-[[[3-(4-Acetyl-3 hydroxy-2-propylphenoxy)propyl]thio]methyl]1,3 oxathiolane-2,2-dipropanoic acid

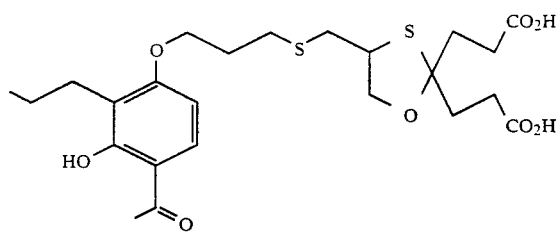

The product of Example 2 (3 g, 0.0052 mol) was dissolved in ethanol (50 ml). Aqueous lithium hydroxide solution (2 M, 9.2 ml) as added and the reaction solution was stirred at room temperature for 3 hrs. Ethanol was removed using the rotary evaporator and the aqueous residue was acidified to pH2 using aqueous 0.5 N sodium bisulfate solution. The oil which separated was extracted with ethyl acetate and the organic layer dried over anhydrous magnesium sulfate. The drying agent was filtered and the filtrate concentrated on the rotary evaporator to give 2.53 g of a colorless oil which was dried at 70° (0.1 mm Hg) for 5 hrs. to give the title compound.

Analysis calculated for $C_{24}H_{34}O_8S_2$: Calc.: C, 56.02; H, 6.67; S, 12.43. Found: C, 56.07; H, 6.85; S, 12.79.

EXAMPLE 4

Diethyl 4-[[[5-(4-acetyl-3-hydroxy-2-propylphenoxy) pentyl]thio]methyl]-1,3-oxathiolane-2,2-dipropanoate

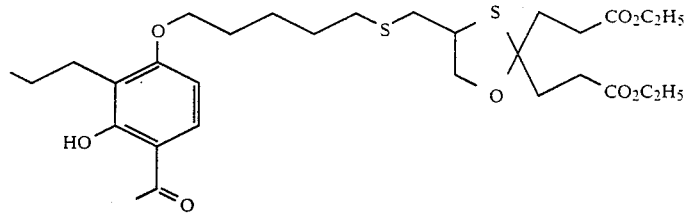

The reaction of the mercaptan from Example 1 (2.0 g, 0.006 mol) and 5 (2-n-propyl-3-hydroxy-4-acetylphenoxy)-1-bromopentane (described in U.S. Pat. No. 4,565,882, Example 1) (2.1 g, 0.06 mol) in methyl ethyl ketone (20 ml) was carried out and worked up in the same manner as described in Example 2. After chromatography on silica gel using 25% ethyl acetate/hexane as eluent, 3.3 g (93%) of the title compound was obtained as an oil.

Analysis calculated for $C_{30}H_{46}O_8S_2$: Calc.: C, 60.18; H, 7.75; S, 10.69. Found: C, 60.01; H, 7.80; S, 10.79.

EXAMPLE 5

4-[[[5-(4-Acetyl-3-hydroxy-2-propylphenoxy)centyl]thio]methyl]-1,3-oxathiolane-2,2-dipropanoic acid

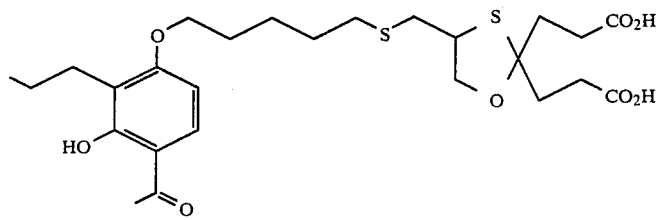

The title compound was prepared according to the procedure of Example 3 using the ester produced in Example 4 (1.0 g, 0.0016 mol) and aqueous lithium hydroxide solution (2 M, 3.0 ml). Following the workup procedure of Example 3, 0.99 g (96%) of the product was obtained as a colorless oil.

Analysis calculated for $C_{26}H_{38}O_8S_2$: Calc.: C, 57.55; H, 7.09; S, 11.79. Found: C, 57.33; H, 7.35; S, 11.68.

EXAMPLE 6

Diethyl 4-[[(3-phenoxypropyl)thio]methyl]-1,3-oxathiolane-2,2-dipropanoate

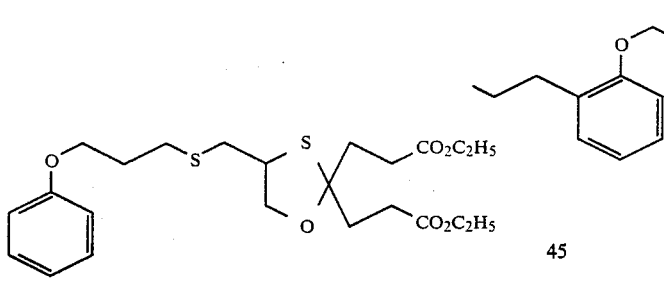

The product of Example 1 (2.0 g, 0.006 mol) and 3-phenoxy-1-bromopropane (1.3 g, 0.006 mol) were dissolved in methyl ethyl ketone (20 ml). Anhydrous potassium carbonate (2.5 g) was added and the reaction was run and worked up as described in the procedure of Example 2. Chromotography of the resulting oil on silica gel using 15% ethyl acetate/hexane as eluent gave 2.70 g (96%) of the title compound as an oil.

Analysis calculated for $C_{23}H_{34}O_6S_2$: Calc.: C, 58.70; H, 7.28; S, 13.60. Found: C, 58.20; H, 7.33; S, 13.24.

EXAMPLE 7

5-(4-Bromobutoxy)-1,2,3,4-tetrahydronaphthalene

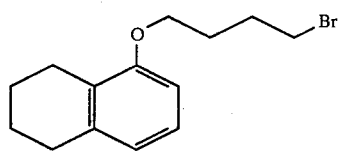

A solution of 5,6,7,8 tetrahydronaphthalene-1-ol (4.2 g, 0.028 mol) in methylene chloride (50 ml) was mixed with a solution of sodium hydroxide (2.3 g, 0.0575 mol) in water (50 ml). After adding tetra-n butylammonium bisulfate (9.6 g, 0.028 mol) and 1,4-dibromobutane (31 g, 0.14 mol), the reaction mixture was refluxed with vigorous stirring for 2 hrs. The reaction was cooled to room temperature, the layers separated and the organic phase washed with saturated sodium chloride solution. After drying over sodium sulfate, the organic phase was concentrated on the rotary evaporator and the residual oil heated under vacuum (0.1 mm Hg) to remove remaining 1,4-dibromobutane. The residue was chromatographed on silica gel using 100% hexane as eluent to give 8.1 g (71%) of the title compound as an oil.

Analysis calculated for $C_{14}H_{19}OBr$: Calc.: C, 59.35; H, 6.70; Br, 28.23. Found: C, 59.11; H, 6.60; Br, 28.71.

EXAMPLE 8

Diethyl 4-[[[5 (2-propylphenoxy)pentyl]thio]methyl]-1,3-oxathiolane-2,2-dipropanoate

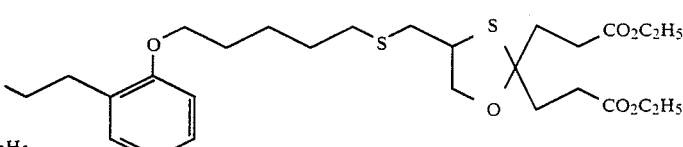

Potassium carbonate (2.5 g) was mixed with a solution of 5-(2-n-propylphenoxy)-1-bromopentane (1.7 g, 0.006 mol) and the product of Example 1 (2.0 g, 0.006 mol) in methyl ethyl ketone (20 ml). The reaction mixture was stirred and refluxed under a nitrogen atmosphere for 4 hrs. and then worked up according to the procedure described in Example 2. The residue was chromatographed on silica gel using 4% acetone/benzene as eluent to give 1.8 g (80%) of the title compound as an oil.

Analysis calculated for $C_{28}H_{44}O_6S_2$; Calc.: C, 62.20; H, 8 20; S, 11.84. Found: C, 62.10; H, 8.35; S, 11.56.

EXAMPLE 9

4-[[[5
(2-Propylphenoxy)pentyl]thio]methyl]-1,3-oxathiolane-
2,2-dipropanoic acid The title compound was prepared according to the procedure of Example 3 using the ester produced in Example 8 (0.80 g, 0.0015 mol) and aqueous lithium hydroxide solution (2 M, 3.0 ml). The product, 0.78 g (89%), was obtained as an oil.

Analysis calculated for $C_{24}H_{36}O_6S_2$: Calc.: C, 59.28; H, 7.48; S, 13.20. Found: C, 59.00; H, 7.60; S, 12.90.

EXAMPLE 10

Diethyl
4-[[[4-[(5,6,7,8-tetrahydro-1-naphthalenyl)oxy]butyl]-
thio]methyl]-1,3-oxathiolane-2,2-dipropanoate The title compound was prepared according to the procedure of Example 2 using the mercaptan produced in Example 1 (2.0 g, 0.006 mol) and the bromide produced in Example 7 (1.7 g, 0.006 mol). The crude product was chromatographed on silica gel using 20% ethyl acetate/hexane as eluent to give 2.5 g (77%) of the product as an oil.

Analysis calculated for $C_{28}H_{42}O_6S_2$: Calc.: C. 61.43; H, 7.86; S. 11.88. Found: C, 61.31; H, 7.81; S, 11.73.

EXAMPLE 11

4-[[[[4-(5,6,7,8-Tetrahydro-1-naphthalenyl)oxy]butyl]-
thio]methyl]-1,3-oxathiolane-2,2-dipropanoic acid The title compound was prepared using the procedure of Example 3 using the ester produced in Example 10 (2.0 g, 0.0037 mol) and aqueous lithium hydroxide solution (2 M, 6.5 ml). The product, 1.78 g (91%) was obtained as an oil.

Analysis calculated for C $_{24}H_{34}O_6S_2$: Calc.: C, 59.73; H, 7.10; S, 13.26. Found: C, 59.89; H, 7.35; S, 13.49.

EXAMPLE 12

1-(3-Bromopropoxy)-2-propylbenzene

The title compound was prepared according to the procedure of Example 7 using 2-n propylphenol (30 g, 0.22 mol) in methylene chloride (400 ml), sodium hydroxide (18.8 g, 0.44 mol) in water (400 ml), 1,3-dibromopropane (100 g, 1 mol) and tetra-n butylammonium bisulfate (80 g, 0.22 mol). Distillation of the crude product yielded 55 g (75%) of pure material, b.p 85°-87° (0.1 mm Hg).

Analysis calculated for $C_{12}H_{17}BrO$: Calc.: C, 56.02; H, 6.66; Br, 31.10. Found: C, 56.00; H, 6.79; Br, 31.42.

EXAMPLE 13

Diethyl
4-[[[3-(2-propylphenoxy)propyl]thio]methyl]1,3
oxathiolane 2,2-dipropanoate The title compound was prepared according to the procedure of Example 2 using the mercaptan produced in Example 1 (2.0 g, 0.006 mol), the bromide produced in Example 12 (1.54 g, 0.006 mol) and anhydrous potassium carbonate (2.5 g). The crude product was chromatographed on silica gel using 15% ethyl acetate/hexane as eluent to give 2.96 g (96%) of the product as an oil.

Analysis calculated for $C_{26}H_{40}O_6S_2$: Calc.: C, 60.91; H, 7.86; S, 12 48. Found: C, 60.88; H, 7.86; S, 12.86.

EXAMPLE 14

4-[[[3-(2-Propylphenoxy)propyl]thio]methyl]-1,3-oxa-
thiolane-2,2-dipropanoic acid The title compound was prepared according to the procedure of Example 3 using the ester produced in Example 13 (2.58 g, 0.005 mol) and aqueous lithium hydroxide solution (2 M, 10 ml). The product, 2.3 g (92%), was obtained as an oil.

Analysis calculated for $C_{22}H_{32}O_6S_2$: Calc.: C, 57.88; H, 7.07; S, 14.02. Found: C, 57.47; H, 7.20; S, 13.91.

EXAMPLE 15

4-[[(3-Phenoxypropyl)thio]methyl]-1,3-oxathiolane-2,2-dipropanoic acid

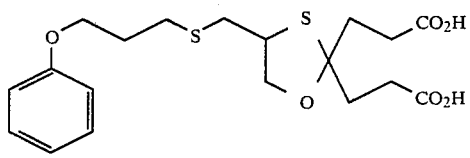

The title compound was prepared according to the procedure of Example 3 using the ester produced in Example 6 (2.44 g, 0.0052 mol) and aqueous lithium hydroxide solution (2 M, 9 ml). The product, 1.86 g (82%), was obtained as an oil.

Analysis calculated for $C_{19}H_{26}O_6S_2$: Calc.: C, 55.06; H, 6.32; S, 15.44. Found: C, 54.78; H, 6.43; S, 15.30

EXAMPLE 16

1-[4-(4-Bromobutoxy)-2-hydroxy-3-propylphenyl]ethanone

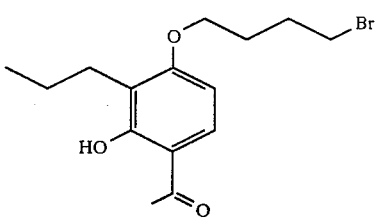

The title compound was prepared according to the procedure of Example 7 using 2,4 dihydroxy-3-n-propylacetophenone (10 g, 0.051 mol) in methylene chloride (100 ml), sodium hydroxide (4.1 g, 0.102 mol) in water (100 ml), 1.4-dibromobutane (38 g, 0.18 mol) and tetra n-butylammonium bisulfate (17.6 g, 0.051 mol). Chromatography of the crude product on silica gel using 15% ethyl acetate/hexane as eluent gave 13.5 g (79%) of the title compound as an oil.

Analysis calculated for $C_{15}H_{21}BrO_3$: Calc.: C, 54.70; H, 6.43; Br, 24.29. Found: C, 54.50; H, 6.29; Br, 24.60.

EXAMPLE 17

Diethyl 4-[[[4-(4-acetyl-3-hydroxy-2-propylphenoxy)butyl]thio]methyl]-1,3-oxathiolane-2,2-dipropanoate

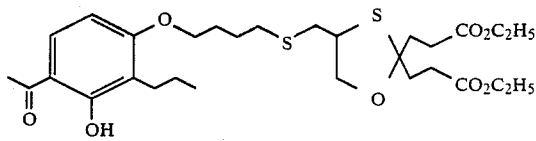

The title compound was prepared according to the procedure of Example 2 using the mercaptan produced in Example 1 (2.0 g, 0.006 mol), the bromide produced in Example 16 (2.35 g, 0.006 mol) and anhydrous potassium carbonate (2.5 g). The crude product was chromatographed on silica gel using 20% ethyl acetate/hexane as eluent to give 3.51 g (98%) of the product as an oil.

Analysis calculated for $C_{29}H_{44}O_8S_2$: Calc.: C, 59.57; H, 7.58; S, 10.94. Found: C, 59.37; H, 7.56; S, 10.57.

EXAMPLE 18

4-[[[4-(4-Acetyl-3-hydroxy-2-propylphenoxy)butyl]thio]methyl]-1,3 oxathiolane-2,2-dipropanoic acid

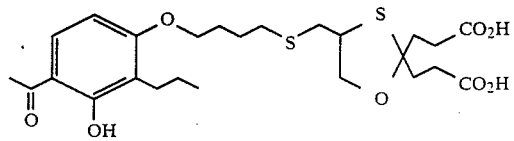

The title compound was prepared according to the procedure of Example 3 using the ester produced in Example 17 (3.23 g, 0.0055 mol) and aqueous lithium hydroxide solution (2 M, 10 ml). The crude product was recrystallized from cyclohexane to give 2.5 g (91%) of the title compound, m.p. 108°–109° C.

Analysis calculated for $C_{25}H_{36}O_8S_2$: Calc.: C, 56.80; H, 6.87; S, 12.10. Found: C, 56.78; H, 7.09; S, 11.80.

EXAMPLE 19

5-[(5-Bromopentyl)oxy]-1,2,3,4-tetrahydronaphthalene

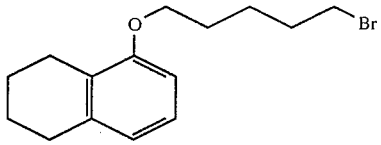

The title compound was prepared according to the procedure of Example 7 using 5,6,7,8 tetrahydro naphthalene-1-ol (8 g, 0.054 mol) in methylene chloride (100 ml), sodium hydroxide (4.32 g, 0.108 mol) in water (100 ml), 1,5-dibromopentane (37 g, 0.19 mol) and tetra n-butylammonium bisulfate (18.3 g, 0.054 mol). Chromatography of the crude product on silica gel using 20% ethyl acetate/hexane as eluent gave 12 g (69%) of the title compound as an oil.

Analysis calculated for $C_{15}H_{21}BrO$: Calc.: C, 60.59; H, 7.12; Br, 26.90. Found: C, 60.12; H, 7.06; Br, 26.42.

EXAMPLE 20

Diethyl 4-[[[5-[(5,6,7,8-tetrahydro-1-naphthalenyl)oxy]pentyl]thio]methyl]-1,3-oxathiolane-2,2-dipropanoate

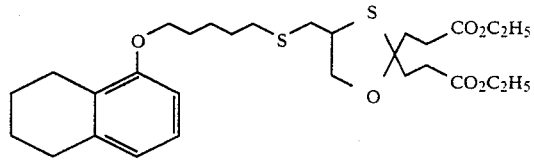

The title compound was prepared according to the procedure of Example 2 using the mercaptan produced in Example 1 (2.0 g, 0.006 mol), the bromide produced in Example 19 (1.78 g, 0.006 mol) and anhydrous potassium carbonate (2.5 g). The crude product was chromatographed on silica gel using 15% ethyl acetate/hexane as eluent to give 3.1 g (88%) of the product as an oil.

Analysis calculated for $C_{29}H_{44}O_6S_2$: Calc.: C, 63.02; H, 8.02; S, 11.58. Found: C, 62.80; H, 8.08; S, 11.61.

EXAMPLE 21

4-[[[5-[(5,6,7,8-Tetrahydro-1-naphthalenyl)oxy]pentyl]thio]methyl]-1,3-oxathiolane-2,2-dipropanoic acid

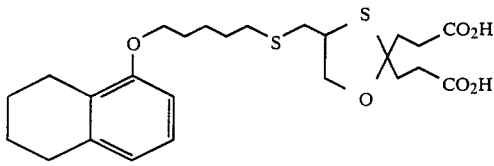

The title compound was prepared according to the procedure of Example 3 using the ester produced in Example 20 (2.8 g, 0.005 mol) and aqueous lithium hydroxide solution (2 M, 9 ml). The crude product slowly crystallized and was recrystallized from ethyl acetate/hexane to give 2.01 g (92%) of the title compound, m.p. 87°–89°.

Analysis calculated for $C_{25}H_{36}O_6S_2$: Calc.: C, 60.46; H, 7.30; S, 12.89. Found: C, 60.08; H, 7.21; S, 12.70.

EXAMPLE 22

1-(4-Bromobutoxy)-2-propylbenzene

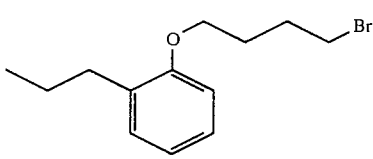

The title compound was prepared according to the procedure of Example 7 using 2 n propylphenol (10 g, 0.073 mol) in methylene chloride (100 ml), sodium hydroxide (6.0 g, 0.146 mol) in water (100 ml), 1,4-dibromobutane (55 g, 0.255 mol) and tetra n butylammonium bisulfate (26 g, 0.073 mol). The crude product was distilled (b.p. 110°–112°/0.25 mm hg) to give 20 g (80%) of the title compound.

Analysis calculated for $C_{13}H_{19}BrO$: Calc.: C, 57.55; H, 7.06; Br, 29.49. Found: C, 57.58; H, 7.06; Br, 29.47.

EXAMPLE 23

Diethyl 4-[[[4-(2-propylphenoxy)butyl]thio]methyl]-1,3-oxathiolane 2,2-dipropanoate

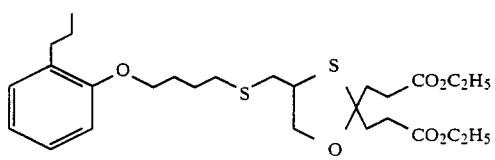

The title compound was prepared according to the procedure of Example 2 using the mercaptan produced in Example 1 (2.0 g, 0.006 mol), the bromide produced in Example 22 (1.63 g, 0.006 mol) and anhydrous potassium carbonate (2.5 g). The crude product was chromatographed on silica gel using 15% ethyl acetate/hexane as eluent to give 2.78 g (87%) of the product as an oil.

Analysis calculated for $C_{27}H_{42}O_6S_2$: Calc.: C, 61.57; H, 8.03; S, 12.15. Found: C, 61.39; H, 8.00; S, 11.93.

EXAMPLE 24

4-[[[4-(2-Propylphenoxy)butyl]thio]methyl]-1,3-oxathiolane-2,2-dipropanoic acid

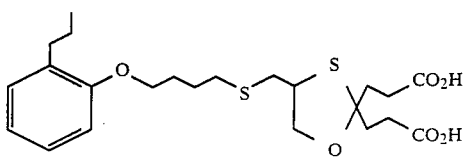

The title compound was prepared according to the procedure of Example 3 using the ester produced in Example 23 (2.0 g, 0.0038 mol) and aqueous lithium hydroxide solution (2M, 6.7 ml). The product, 1.8 g (90%), was obtained as an oil.

Analysis calculated for $C_{23}H_{34}O_6S_2$: Calc.: C, 58.70; H, 7.28; S, 13.60. Found: C, 58.43; H, 7.36; S, 13.58.

EXAMPLE 25

1-[4-(2-Bromoethoxy)-2-hydroxy-3-propylphenyl]ethanone

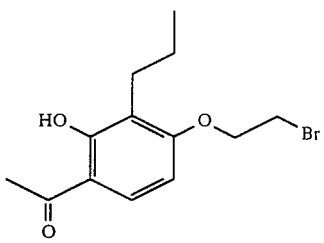

The title compound was prepared according to the procedure of Example 7 using 2,4-dihydroxy-3-n-propylacetophenone (5 g, 0.025 mol) in methylene chloride (50 ml), sodium hydroxide (2 g, 0.05 mol) in water (50 ml), 1,2-dibromoethane (17 g, 0.088 mol) and tetra-n-butylammonium bisulfate (8.7 g, 0.025 mol). Chromatography of the crude product on silica gel using 15% ethyl acetate/hexane as eluent gave 13.5 g (79%) of the title compound as an oil.

Analysis calculated for $C_{13}H_{17}BrO_3$: Calc.: C, 51.82; H, 5.69; Br, 26.55. Found: C, 51.86; H, 5.81; Br, 26.44.

EXAMPLE 26

Diethyl 4[[[2-(4-acetyl-3-hydroxy-2-propylphenoxy)ethyl]thio]methyl]-1,3-oxathiolane-2,2-dipropanoate

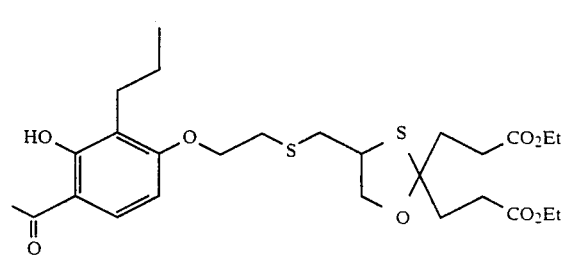

The title compound was prepared according to the procedure of Example 2 using the mercaptan produced in Example 1 (2.0 g, 0.006 mol), the bromide produced in Example 25 (1.80 g, 0.006 mol) and anhydrous potassium carbonate (2.5 g). The crude product was chromatographed on silica gel using 20% ethyl acetate/hexane as eluent to give 3.25 g (91%) of the product as an oil.

Analysis calculated for $C_{27}H_{40}O_8S_2$: Calc.: C, 58.26; H, 7.24; S, 11.49. Found: C, 57.91; H, 7.28; S, 11.49.

EXAMPLE 27

4-[[[2-(4-Acetyl-3-hydroxy-2-propylphenoxy)ethyl]thio]methyl]-1,3-oxathiolane-2,2-dipropanoic acid

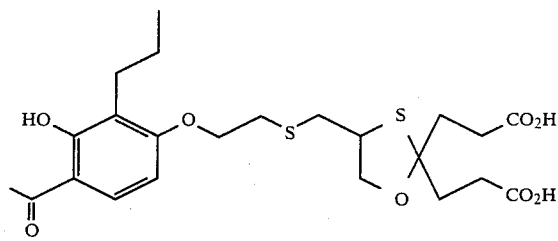

The title compound was prepared according to the procedure of Example 3 using the ester produced in Example 26 (2.75 g, 0.005 mol) and aqueous lithium hydroxide solution (2M, 8.5 ml). The crude product was recrystallized from ethyl acetate/hexane to give 2.3 g (92%) of the title compound, m.p. 109°–111° C.

Analysis calculated for $C_{23}H_{32}O_8S_2$: Calc.: C, 55.13; H, 6.44; S, 12.77. Found: C, 54.99; H, 6.73; S, 12.31.

EXAMPLE 28

5-(3-Bromopropoxy)-1,2,3,4-tetrahydronaphthalene

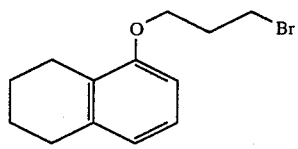

The title compound was prepared according to the procedure of Example 7 using 5,6,7,8-tetrahydronaphthalene-1-ol (10 g, 0.067 mol) in methylene chloride (100 ml), sodium hydroxide (5.5 g, 0.134 mol) in water (100 ml), 1,3-dibromopropane (47 g, 0.23 mol) and tetra n-butylammonium bisulfate (23 g, 0.067 mol). Chromatography of the crude product on silica gel using 1% ethyl acetate/hexane as eluent gave 12 g (60%) of the title compound as an oil.

Analysis calculated for $C_{13}H_{17}BrO$: Calc.: C, 57.98; H, 6.36; Br, 29.70. Found: C, 58.22; H, 6.47; Br, 29.83.

EXAMPLE 29

Diethyl 4-[[[3-[(5,6,7,8-tetrahydro-1-naphthalenyl)oxy]propyl]thio]methyl]-1,3-oxathiolane-2,2-dipropanoate

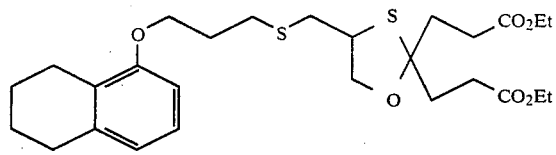

The title compound was prepared according to the procedure of Example 2 using the mercaptan produced in Example 1 (2.1 g, 0.006 mol), the bromide produced in Example 28 (1.89 g, 0.0065 mol) and anhydrous potassium carbonate (2.5 g). The crude product was chromatographed on silica gel using 20% ethyl acetate/hexane as eluent to give 3.1 g (91%) of the product as an oil.

Analysis calculated for $C_{27}H_{40}O_6S_2$: Calc.: C, 61.81; H, 7.69; S, 12.20. Found: C, 61.52; H, 7.77; S, 11.88.

EXAMPLE 30

4-[[[3-[(5,6,7,8-Tetrahydro-1-naphthalenyl)oxy]propyl]thio]methyl]-1,3-oxathiolane-2,2-dipropanoic acid

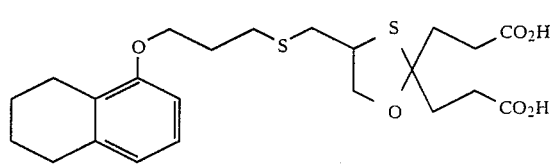

The title compound was prepared according to the procedure of Example 3 using the ester produced in Example 29 (2.6 g, 0.005 mol) and aqueous lithium hydroxide solution (2M, 8.5 ml). The product, 2.45 g (94%), was obtained as an oil.

Analysis calculated for $C_{23}H_{32}O_6S_2$: Calc.: C, 57.96; H, 6.88; S, 13.62. Found: C, 57.99; H, 7.15; S, 13.62.

EXAMPLE 31

Diethyl-4-(mercaptomethyl)-1,3-dithiolane-2,2-dipropanoate

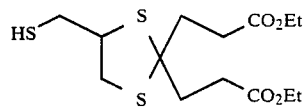

A stirred solution of 1,2,3-trimercaptopropane (10.0 g, 0.071 mol) and diethyl 4-oxopimelate (16.43 g, 0.071 mol) in methylene chloride (300 ml) under nitrogen atmosphere was treated with boron trifluoride etherate (2 ml). After stirring for 3 days at room temperature, the reaction was quenched by addition of 200 ml of 5% sodium bicarbonate solution. The organic phase was separated and dried over anhydrous sodium sulfate. The drying agent was filtered and the filtrate concentrated on the rotary evaporator. The residue was chromatographed on silica gel using 5% ethyl acetate/hexane as eluent to give 10 g (40%) of the title compound as an oil.

Analysis calculated for $C_{14}H_{24}O_4S_3$: Calc.: C, 47.72; H, 6.87; S, 27.25. Found: C, 47.89; H, 6.92; S, 27.69.

EXAMPLE 32

Diethyl 4-[[[5-(4-acetyl-3-hydroxy-2-propylphenoxy)pentyl]thio]methyl]-1,3-dithiolane-2,2-dipropanoate

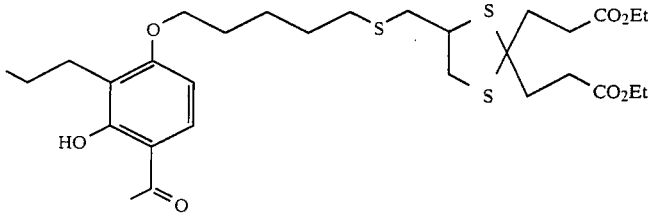

The title compound was prepared according to the procedure of Example 2 using the mercaptan produced in Example 31 (0.5 g, 0.0014 mol), 5-(2-n-propyl-3-hydroxy-4-acetylphenoxy)-1-bromopentane (described in U.S. Pat. No. 4,565,882, Example 1) (0.484 g, 0.0014 mol) and anhydrous potassium carbonate (0.70 g) in methyl ethyl ketone (5 ml). The crude product was chromatographed on silica gel using 30% ethyl acetate/hexane as eluent to give 0.52 g (75%) of the product as an oil.

Analysis calculated for $C_{30}H_{46}O_7S_3$: Calc.: C, 58.61; H, 7.54; S, 15.62. Found: C, 58.22; H, 7.66; S, 15.90.

EXAMPLE 33

4-[[[5-(4-Acetyl-3-hydroxy-2-propylphenoxy)pentyl]thio]methyl]-1,3-dithiolane-2,2-dipropanoic acid

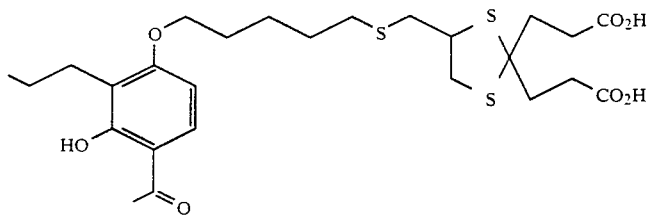

The title compound was prepared according to the procedure of Example 3 using the ester produced in Example 32 (0.48 g, 0.00078 mol) and aqueous lithium hydroxide solution (2M, 1.5 ml). The crude product was chromatographed on silica gel using 3% ethyl acetate/toluene (containing 0.5% acetic acid). The product, 0.40 g, was obtained as a viscous oil containing two molar equivalents of acetic acid.

Analysis calculated for $C_{26}H_{38}O_7S_3 \cdot 2HOAc$: Calc.: C, 53.08; H, 6.83; S, 14.14. Found: C, 52.87; H, 6.98; S, 14.33.

EXAMPLE 34

Diethyl 4-[[[3-(4-acetyl-3-hydroxy-2-propylphenoxy)propyl]thio]methyl]-1,3-dithiolane-2,2-dipropanoate

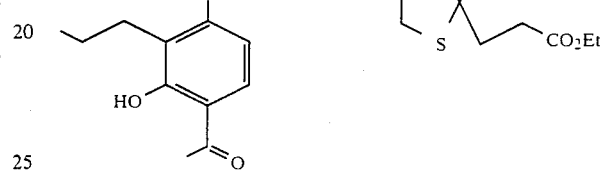

The title compound was prepared according to the procedure of Example 2 using the mercaptan produced in Example 31 (2.0 g, 0.0056 mol), 3-(2-n-propyl-3-hydroxy-4-acetylphenoxy)-1-bromopropane (prepared as described in U.S. Pat. No. 4,565,882, Example 14) (2.0 g, 0.006 mol) and anhydrous potassium carbonate (3.5 g) in methyl ethyl ketone (25 ml) at reflux overnight. The crude product was chromatographed on silica gel using 20% ethyl acetate/hexane as eluent to give 2.1 g (70%) of the product as an oil.

Analysis calculated for $C_{28}H_{42}O_7S_3$: Calc.: C, 57.32; H, 7.21; S, 16.43. Found: C, 57.18; H, 7.30; S, 16.68.

EXAMPLE 35

4-[[[3-(4-Acetyl-3-hydroxy-2-propylphenoxy)propyl]thio]methyl]-1,3-dithiolane-2,2-dipropanoic acid

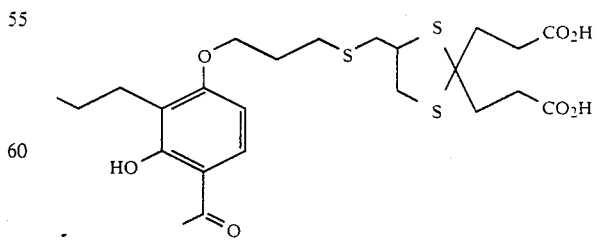

The title compound was prepared according to the procedure of Example 3 using the ester produced in Example 34 (1.5 g, 0.0025 mol) and aqueous lithium hydroxide solution (2M, 5 ml). The crude product was chromatographed o silica gel using 40% ethyl acetate/hexane/0.5% acetic acid as eluent to give 1.1 g of product as an oil. The oily product was azeotroped twice with toluene to give the title compound containing 0.5 mol of toluene. The toluene was removed by heating at 100° C. under vacuum (0.1 mm Hg) for 4 hrs.

Analysis calculated for $C_{24}H_{34}O_7S_3$: Calc.: C, 54.33; H, 6.46; S, 18.09. Found: C 54 64; H, 6.51; S, 18.01.

EXAMPLE 36

Ethyl 4-(mercaptomethyl)-2-methyl-1,3-oxathiolane-2-propanoate

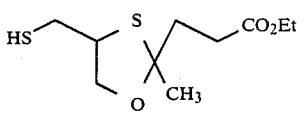

A stirred solution of 2,3-dimercapto-1-propanol (20.0 g, 0.161 mol) and ethyl levulinate (22 g, 0.161 mol) in methylene chloride (600 ml) under a nitrogen atmosphere was treated with boron trifluoride etherate (5 ml). After stirring for 3 days at room temperature, the reaction was quenched by addition of 250 ml of 5% potassium bicarbonate solution. The organic phase was separated and dried over anhydrous sodium sulfate. The drying agent was filtered and the filtrate concentrated on the rotary evaporator. The residue was chromatographed on silica gel using 6% ethyl acetate/hexane as eluent to give 17 g (43%) of the title compound as an oil.

Analysis calculated for $C_{10}H_{18}S_2O_3$: Calc.: C, 47.99; H, 7.25; S, 25.57. Found: C, 48.01; H, 7.40; S, 25.89.

EXAMPLE 37

Ethyl 4-[[[3-(4-acetyl-3-hydroxy-2-propylphenoxy)propyl]thio]methyl]-2-methyl-1,3-oxathiolane-2-propanoate

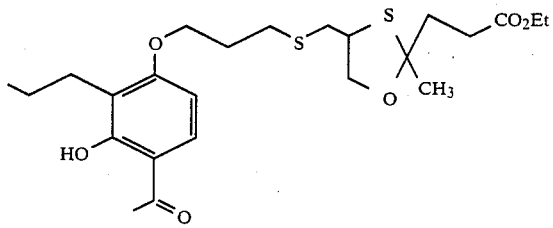

The title compound was prepared according to the procedure of Example 2 using the mercaptan produced in Example 36 (1.5 g, 0.006 mol), 3-(2-n-propyl-3-hydroxy-4-acetylphenoxy)-1-bromopropane (1.9 g, 0.006 mol) and anhydrous potassium carbonate (2.5 g). The crude product was chromatographed on silica gel using 20% ethyl acetate/hexane as eluent to give 2.7 g (93%) of the product as an oil.

Analysis calculated for $C_{24}H_{36}O_6S_2$: Calc.: C, 59.48; H, 7.49; S, 13.20. Found: C, 59.26; H, 7.61; S, 13.03.

EXAMPLE 38

4-[[[3-(4-Acetyl-3-hydroxy-2-propylphenoxy)propyl]thio]methyl]-2-methyl-1,3-oxathiolane-2-propanoic acid

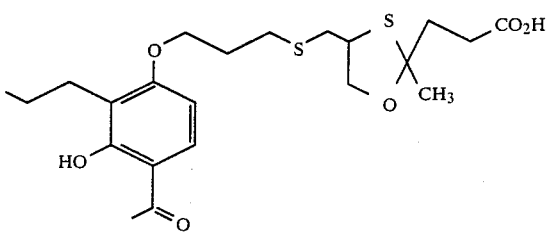

The title compound was prepared according to the procedure of Example 3 using the ester produced in Example 37 (2.2 g, 0.0043 mol) and aqueous lithium hydroxide solution (2M, 6 ml). The product, 2.05 g (90%), was obtained as an oil.

Analysis calculated for $C_{22}H_{32}O_6S_2$: Calc.: C, 57.88; H, 7.07; S, 14.02. Found: C, 57.62; H, 7.20; S, 13.92.

EXAMPLE 39

Diethyl 4-[[[3-(4-acetyl-3-hydroxy-2-propylphenoxy)-2-hydroxypropyl]thio]methyl]-1,3-oxathiolane-2,2-dipropanoate

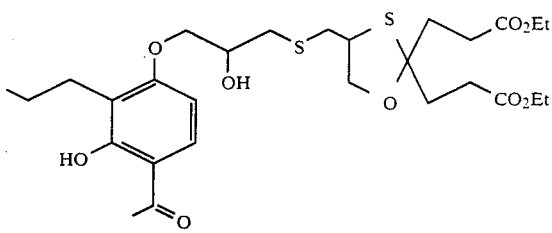

The title compound was prepared according to the procedure of Example 2 using the mercaptan produced in Example 1 (2.0 g, 0.0066 mol), 3-(2-n-propyl-3-hydroxy-4-acetylphenoxy)-1,2-epoxypropane (described in U.S. Pat. No. 4,565,882) (1.5 g, 0.006) and anhydrous potassium carbonate (3.0 g). The crude product was chromatographed on silica gel using 40% ethyl acetate/hexane as eluent to give 3.22 g (92%) of the product as an oil.

Analysis calculated for $C_{28}H_{42}O_9S_2$: Calc.: C, 57.32; H, 7.21; S, 10.90. Found: C, 57.25; H, 7.28; S, 10.53.

EXAMPLE 40

4-[[[3-(4-Acetyl-3-hydroxy-2-propylphenoxy)-2-hydroxypropyl]thio]methyl]-1,3-oxthiolane-2,2-dipropanoic acid

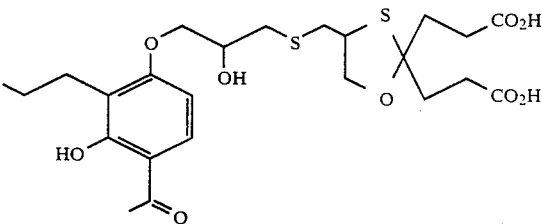

The title compound was prepared according to the procedure of Example 3 using the ester produced in Example 39 (2.67 g, 0.0045 mol) and aqueous lithium hydroxide solution (2M, 8.5 ml). The product, 2.2 g (91%), was obtained as an oil.

Analysis calculated for $C_{24}H_{34}O_9S_2$: Calc.: C, 54.33; H, 6.46; S, 12.06. Found: C, 54.61; H, 6.86; S, 11.62.

EXAMPLE 41

Ethyl 4-[[[4-(4-acetyl-3-hydroxy-2-propylphenoxy)butyl]thio]methyl]-2-methyl-1,3-oxathiolane-2-propanoate

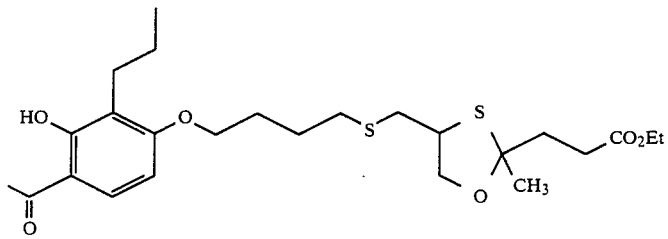

The title compound was prepared according to the procedure of Example 2 using the mercaptan produced in Example 36 (1.5 g, 0.006 mol), the bromide produced in Example 16 (2.0 g, 0.006 mol) and anhydrous potassium carbonate (2.5 g). The crude product was chromatographed on silica gel using 20% ethyl acetate/hexane as eluent to give 2.73 g (91%) of the product as an oil.

Analysis calculated for $C_{25}H_{38}O_6S_2$: Calc.: C, 60.22; H, 7.68; S, 12.84. Found: C, 60.19; H, 7.83; S, 13.04.

EXAMPLE 42

4-[[[4-(4-Acetyl-3-hydroxy-2-propylphenoxy)butyl]thio]methyl]-2-methyl-1,3-oxathiolane-2-propanoic acid

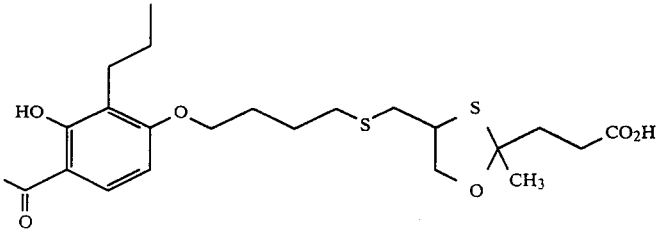

The title compound was prepared according to the procedure of Example 3 using the ester produced in Example 41 (2.7 g, 0.0052 mol) and aqueous lithium hydroxide solution (2M, 8.5 ml). The product, 2.23 g (91%), was obtained as an oil.

Analysis calculated for $C_{23}H_{34}O_6S_2$: Calc.: C, 58.70; H, 7.28; S, 13.60. Found: C, 58.44; H, 7.30; S, 13.40.

EXAMPLE 43

Diethyl 5-(hydroxymethyl)-1,3-oxathiolane-2,2-dipropanoate

The title compound was prepared according to the procedure of Example 1 using 3-mercapto-1,2-propanediol (10.8 g, 0.1 mol), diethyl 4-oxopimelate (23 g, 0.1 mol) and boron trifluoride etherate (2.5 ml) in methylene chloride (300 ml). The crude product was chromatographed on silica gel using 40% ethyl acetate/hexane as eluent to give 14.5 g (45%) of product.

Analysis calculated for $C_{14}H_{24}O_6S$: Calc.: C, 52.49; H, 7.55; S, 9.99. Found: C, 52.61; H, 7.71; S, 10.10.

EXAMPLE 44

Diethyl 4-[[[4-(4-acetyl-3-hydroxy-2-propylphenoxy)butyl]thio]methyl]-1,3-dithiolane-2,2-dipropanoate

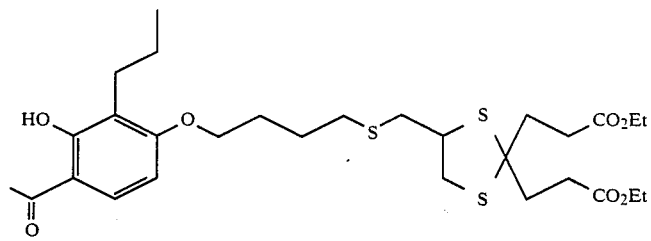

The title compound was prepared according to the procedure of Example 2 using the mercaptan produced in Example 31 (2.0 g, 0 0056 mol), the bromide produced in Example 16 (2.0 g, 0.0065 mol) and anhydrous potassium carbonate (2.5 g). The crude product was chromatographed on silica gel using 20% ethyl acetate/hexane as eluent to give 1.56 g (60%) of the product as an oil.

Analysis calculated for $C_{29}H_{44}O_7S_3$: Calc.: C, 57.98; H, 7.38; S, 15.98. Found: C, 57.95; H, 7.48; S, 15.59.

EXAMPLE 45

4-[[[4-(4-Acetyl-3-hydroxy-2-propylphenoxy)butyl]thio]methyl]-1,3-dithiolane-2,2-dipropanoic acid, ethyl acetate salt

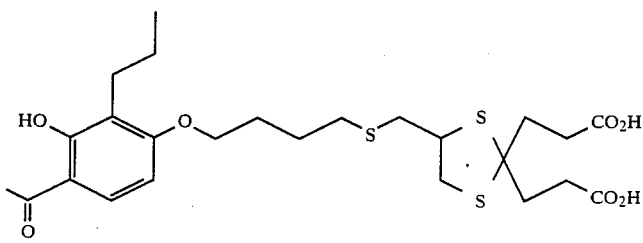

The title compound was prepared according to the procedure of Example 3 using the ester produced in Example 44 (1.0 g, 0.00167 mol) and aqueous lithium hydroxide solution (2M, 3.5 ml). The product, 0.90 g (85%), was obtained as a viscous oil containing one molar equivalent of ethyl acetate.

Analysis calculated for $C_{25}H_{36}O_7S_3 \cdot C_4H_8O_2$: Calc.: C, 53.53; H, 6.84; S, 16.32. Found: C, 53.67; H, 6.72; S, 16.14.

EXAMPLE 46

4-[[[3-(4-Acetyl-3-hydroxy-2-propylphenoxy)propyl]sulfinyl]methyl]-1,3-dithiolane-2,2-dipropanoic acid

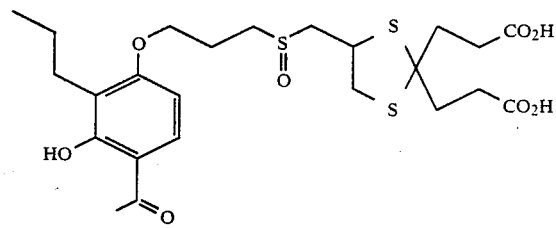

To a cold (0° C.), stirred solution of the sulfide from Example 35 (0.25 g, 0.00047 mol) in methylene chloride (5 ml) was added 85% m chloroperbenzoic acid (0.081 g, 0.00047 mol). After stirring 2 hrs. at 0° C., the solvent was evaporated using a nitrogen stream and the residue chromatographed on silica gel using ethyl acetate containing 0.5% acetic acid as eluent. The title compound (0.20 g, 75%) was obtained as an oil.

Analysis calculated for $C_{24}H_{34}O_8S_3$: Calc.: C, 51.57; H, 6.27; S, 17.16. Found: C, 51.24; H, 6.35; S, 16.83.

EXAMPLE 47

Ethyl 4-(mercaptomethyl)-2-methyl-1,3-dithiolane-2-propanoate

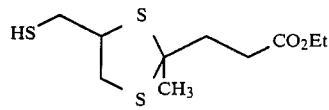

The title compound was prepared according to the procedure of Example 1 using 1,2,3-trimercaptopropane (5.6 g, 0.04 mol), ethyl levulinate (5.8 g, 0.04 mol) and boron trifluoride etherate (1.25 ml) in methylene chloride (150 ml). The crude product was chromatographed on silica gel using 5% ethyl acetate/hexane as eluent to give 3.35 g (31%) of product.

Analysis calculated for $C_{10}H_{18}O_2S_3$: Calc.: C, 45.11; H, 6.81; S, 36.06. Found: C, 45.56; H, 6.82; S, 36.42.

EXAMPLE 48

Ethyl 4-[[[3-(4-acetyl-3-hydroxy-2-propylphenoxy)propyl]thio]methyl]-2-methyl-1,3-dithiolane-2-propanoate The title compound was prepared according to the procedure of Example 2 using the mercaptan produced in Example 47 (1.5 g, 0.0056 mol), 3 (2-n-propyl-3-hydroxy-4-acetylphenoxy)-1-bromopropane (described in U.S. Pat. No. 4,565,882, Example 14) (1.8 g, 0.006 mol) and anhydrous potassium carbonate (2.5 g). The crude product was chromatographed on silica gel using 15% ethyl acetate/hexane as eluent to give 1.85 g (60%) of the product as an oil.

Analysis calculated for $C_{24}H_{36}O_5S_3$: Calc.: C, 56.54; H, 7.42; S, 19.65. Found: C, 56.94; H, 7.41; S, 19.39.

EXAMPLE 49

Ethyl 4-[[[3-(4-acetyl-3-hydroxy-2-propylphenoxy)-2-hydroxypropyl]thio]methyl]-2-methyl-1,3-dithiolane-2-propanoate

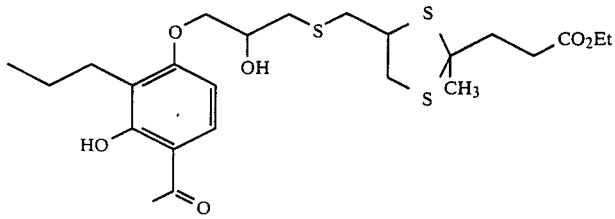

The title compound was prepared according to the procedure of Example 2 using the mercaptan produced in Example 47 (1.5 g, 0.006 mol), 3-(2-n-propyl-3-hydroxy-4-acetylphenoxy)-1,2-epoxypropane (described in U.S. Pat. No. 4,565,882) (1.4 g, 0.006 mol) and anhydrous potassium carbonate (2.5 g). The crude product was chromatographed on silica gel using 35% ethyl acetate/hexane as eluent to give 1.7 g (65%) of the product as an oil.

Analysis calculated for $C_{24}H_{36}O_6S_3$: Calc.: C, 54.75; H, 7.19; S, 19.01. Found: C, 55.07; H, 7 29; S, 18 98.

EXAMPLE 50

4-[[[3-(4-Acetyl-3-hydroxy-2-propylphenoxy)propyl]thio]methyl]-2-methyl-1,3-dithiolane-2-propanoic acid

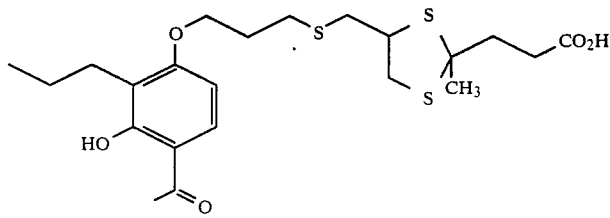

The title compound was prepared according to the procedure of Example 3 using the ester produced in Example 48 (1.5 g, 0.003 mol) and aqueous lithium hydroxide solution (2M, 3.5 ml). The product, 1.4 g (90%), was obtained as a viscous oil containing 0.33 molar equivalent of ethyl acetate.

Analysis calculated for $C_{22}H_{32}O_5S_3 \cdot 0.33C_4H_8O_2$: Calc.: C, 55.83; H, 6.96; S, 19.12. Found: C, 55.55; H, 6.88; S, 18.99.

EXAMPLE 51

4-[[[3-(4-Acetyl-3-hydroxy-2-propylphenoxy)-2-hydroxypropyl]thio]methyl]-2-methyl-1,3-dithiolane-2-propanoic acid

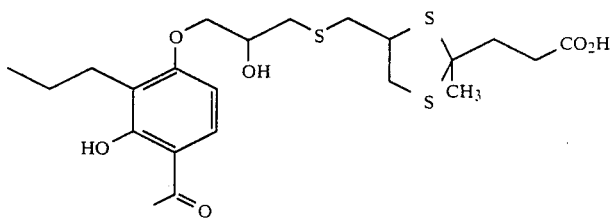

The title compound was prepared according to the procedure of Example 3 using the ester produced in Example 49 (1.3 g, 0.0025 mol) and aqueous lithium hydroxide solution (2M, 10 ml). The product, 1.27 g (97%), was obtained as a viscous oil.

Analysis calculated for $C_{22}H_{32}O_6S_3$: Calc.: C, 54.00; H, 6.60; S, 19.65. Found: C, 53.68; H, 6.90; S, 19.89.

EXAMPLE 52

4-[[[3-(4-Acetyl-3-hydroxy-2-propylphenoxy)propyl]sulfinyl]methyl]-2-methyl-1,3-oxathiolane-2-propanoic acid.

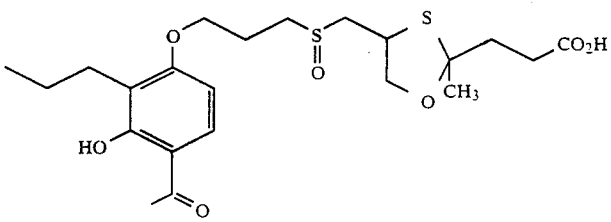

The title compound was prepared according to the procedure of Example 46 using the sulfide obtained in Example 38 (0.30 g, 0.00066 mol) and m-chloroperbenzoic acid (0.113 g, 0.00066 mol). The crude product was chromatographed on silica gel using ethyl acetate containing 0.5% acetic acid to give 0.157 g (50%) of the desired product as an oil.

Analysis calculated for $C_{22}H_{32}O_7S_2$: Calc.: C, 55.88; H, 6.82; S, 13.53. Found: C, 55.52; H, 6.87; S, 13.07.

EXAMPLE 53

Separation Of Racemates Of Example 37

The racemates of Example 37 were separated on HPLC using a 500×9 mm column of Cyclobond B and 55/45 methanol/water as eluent. Repetitive injections yielded 68 mg of racemate A and 84 mg of racemate B.

EXAMPLE 54

Saponification of racemate A to racemic acid.

Racemic acid was prepared according to the procedure of Example 3 using racemate A produced in Example 53 (0.068, 0.00014 mol) and aqueous lithium hydroxide solution (2M, 0.2 ml). The product (0.054 g, 85%), one of the two racemates obtained in Example 38, was obtained as an oil.

Analysis calculated for $C_{22}H_{32}O_6S_2$: Calc.: C, 57.88; H, 7.07; S, 14.02. Found: C, 57.71; H, 7.05; S, 13.99.

EXAMPLE 55

Saponification of racemate B to racemic acid.

Racemic acid was prepared according to the procedure of Example 3 using racemate B produced in Example 53 (0.084, 0.0002 mol) and aqueous lithium hydroxide solution (2 M, 0.3 ml). The product (0.072 g, 90%), one of the two racemates obtained in Example 38, was obtained as an oil.

Analysis calculated for $C_{22}H_{32}O_6S_2$: Calc.: C, 57.88; H, 7.07; S, 14.02. Found: C, 57.81; H, 7.03; S, 13.89.

EXAMPLE 56

Diethyl 4-[[[3-(4-acetyl-3-hydroxy-2-propylphenoxy)-2-hydroxypropyl]thio]methyl]-1,3-dithiolane-2,2-dipropanoate The title compound was prepared according to the procedure of Example 2 using the mercaptan produced in Example 31 (1.5 g, 0.004 mol), 3-(2-n-propyl-3-hydroxy-4-acetylphenoxy)-1,2-epoxypropane (described in U.S. Pat. No. 4,565,882) (1.1 g, 0.004 mol) and anhydrous potassium carbonate (1.75 g) in methyl ethyl ketone (15 ml). The crude product was chromatographed on silica gel using 30% ethyl acetate/hexane as eluent to give 1.9 g (60%) of the product as an oil.

Analysis calculated for $C_{28}H_{42}O_8S_3$: Calc.: C, 55.80; H, 7.02; S, 15.93. Found: C, 55.42; H, 6.87; S, 15.63.

EXAMPLE 57

4-[[[3-(4-Acetyl-3-hydroxy-2-propylphenoxy)-2-hydroxypropyl]thio]methyl]-1,3-dithiolane-2,2-dipropanoic acid

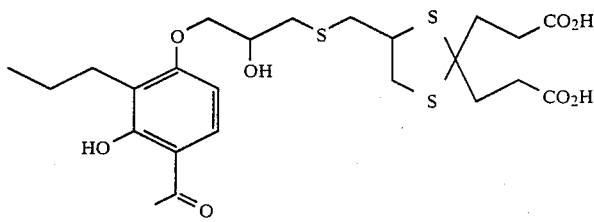

The title compound was prepared according to the procedure of Example 3 using the ester produced in Example 56 (1.9 g, 0.0031 mol) and aqueous lithium hydroxide solution (2M, 7.8 ml). The product, 1.4 g (85%), was obtained as an oil containing 0.33 molar equivalent of ethyl acetate.

Analysis calculated for $C_{24}H_{34}O_8S_3 \cdot 0.33\ C_4H_8O_2$: Calc.: C, 52.74; H, 6.41; S, 16.67. Found: C, 52 53; H, 6.60; S, 16.39.

EXAMPLE 58

Methyl 4-acetylbutyrate

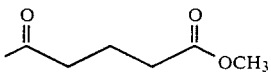

To a rapidly stirred slurry of sodium bicarbonate (25 g) in a solution of 4-acetylbutyric acid (13 g, 0.1 mol) in dimethylformamide (150 ml) was added methyl iodide (47 g). After stirring overnight at room temperature under nitrogen, the reaction mixture was diluted with water (300 ml) and extracted with ethyl ether (250 ml). The organic phase was washed with water and dried over sodium sulfate. The drying agent was filtered and the filtrate concentrated on the rotary evaporator to give 12 g of the title compound as a light yellow oil. The product can be purified by distillation: b.p. 59°–60° (0.1 mm Hg).

EXAMPLE 59

Methyl 4-(mercaptomethyl)-2-methyl-1,3-dithiolane-2-butanoate

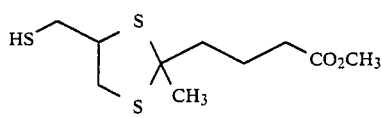

The title compound was prepared according to the procedure of Example 1 using 1,2,3-trimercaptopropane (5 g, 0.0355 mol), methyl 4-acetylbutyrate (5.1 g, 0.0355 mol) and boron trifluoride etherate (1 ml) in methylene chloride (125 ml). The crude product was chromatographed on silica gel using 5% ethyl acetate/hexane as eluent to give 6.5 g (69%) of product.

Analysis calculated for $C_{10}H_{18}O_2S_3$: Calc. C, 45.11; H, 6.81; S, 36.05. Found: C, 45.01; H, 7.03; S, 36.38.

EXAMPLE 60

Methyl 4-[[[3-(4-acetyl-3-hydroxy-2-propylphenoxy)propyl]thio]methyl]-2-methyl-1,3-dithiolane-2-butanoate

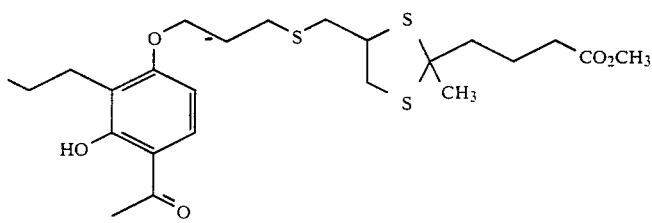

The title compound was prepared according to the procedure of Example 2 using the mercaptan produced in Example 59 (1.2 g, 0.0045 mol), 3-(2-n-propyl-3-hydroxy-4-acetylphenoxy)-1-bromopropane (described in U.S. Pat. No. 4,565,882, Example 14) (1.4 g, 0.006 mol) and anhydrous potassium carbonate (2.5 g). The crude product was chromatographed on silica gel using 15% ethyl acetate/hexane as eluent to give 2.15 g (96%) of the product as an oil.

Analysis calculated for $C_{24}H_{36}O_5S_3$: Calc.: C, 57.58; H, 7.25; S, 19.18. Found: C, 57.56; H, 7.38; S, 19.54.

EXAMPLE 61

4-[[[3-(4-Acetyl-3-hydroxy-2-propylphenoxy)propyl]thio]methyl]-2-methyl-1,3-dithiolane-2-butanoic acid

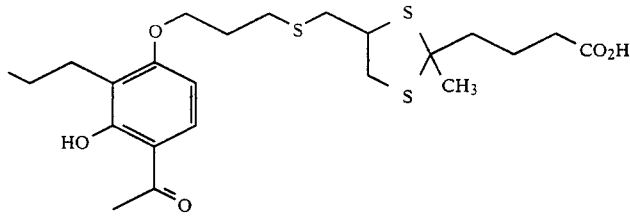

The title compound was prepared according to the procedure of Example 3 using the ester produced in Example 60 (2.0 g, 0.004 mol) and aqueous lithium hydroxide solution (2M, 5 ml). The product, 1.87 g (96%), was obtained as an oil containing 0.33 molar equivalent of ethyl acetate. The ethyl acetate was removed by drying at 100° C. for 4 hrs. under vacuum (0.1 mm Hg).

Analysis calculated for $C_{23}H_{34}O_5S_3$: Calc.: C, 56.77; H, 7.04; S, 19.73. Found: C, 56.64; H, 7.14; S, 19.88.

EXAMPLE 62

Diethyl 5-[[[(4-methylphenyl)sulfonyl]oxy]1,3-oxathiolane-2,2-dipropanoate

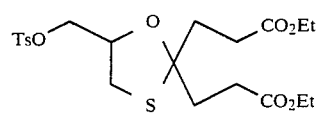

To a cold (0°) stirred solution of the alcohol produced in Example 43 (3.0 g, 0.0093 mol) in pyridine (30 ml) was added p-toluenesulfonyl chloride (2.5 g) in portions over 15 minutes. When addition was completed, the reaction was stirred at room temperature for 2 hrs. The reaction mixture was diluted with ether and washed with water, 0.5N aqueous sodium bisulfate solution, 5% aqueous sodium bicarbonate solution and water. The organic layer was dried over sodium sulfate, filtered, and the filtrate concentrated on the rotary evaporator to give 4.4 g (97%) of the title compound as a light yellow oil.

Analysis calculated for $C_{21}H_{30}O_8S_2$: Calc.: C, 53.16; H, 6.37; S, 13.49. Found: C, 53.41; H, 6.11; S, 13.69.

EXAMPLE 63

Diethyl 5-[(acetylthio)methyl]-1,3-oxathiolane-2,2-dipropanoate

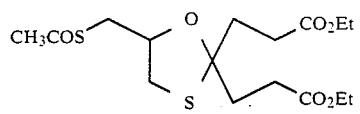

A stirred slurry of potassium thioacetate (0.50 g) in a solution of the tosylate produced in Example 62 (2.0 g, 0.0042 mol) in acetone (20 ml) was refluxed under nitrogen for 5 hrs. The reaction mixture was filtered and the filtrate concentrated on the rotary evaporator. The residue was dissolved in ethyl acetate, washed with water and dried over sodium sulfate. The drying agent was filtered, the solvent removed using the rotary evaporator and the residue chromatographed on silica gel using 10% ethyl acetate/hexane as eluent to give 1.1 g (72%) of the title compound as a light yellow oil.

Analysis calculated for $C_{16}H_{26}O_6S_2$: Calc.: C, 50.78; H, 6.92; S, 16.91. Found: C, 50.71; H, 7.05; S, 17.10.

EXAMPLE 64

Diethyl 5-(mercaptomethyl)-1,3-oxthiolane-2,2-dipropanoate

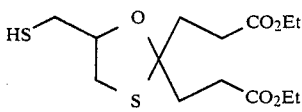

A solution of sodium ethoxide in ethanol (20 mls) [prepared from 0.16 g (0.006 g-atom) of sodium metal] and the thioacetate produced in Example 63 (2.1 g, 0.0055 mol) was stirred for one hour at room temperature under nitrogen. Ethanol was removed in vacuo on the rotary evaporator and the residue dissolved in ethyl acetate. This organic phase was washed with 0.5N sodium bisulfate solution and dried over sodium sulfate. The drying agent was filtered and the filtrate concentrated on the rotary evaporator to give 1.97 g (95%) of the title compound as an oil.

Analysis calculated for $C_{14}H_{24}O_5S_2$: Calc.: C, 48.99; H, 7.19; S, 19.03. Found: C, 48.99; H, 7.12; S, 19.52.

EXAMPLE 65

Diethyl 5-[[[3-(4-acetyl-3-hydroxy-2-propylphenoxy)propyl]thio]methyl]-1,3-oxathiolane-2,2-dipropanoate

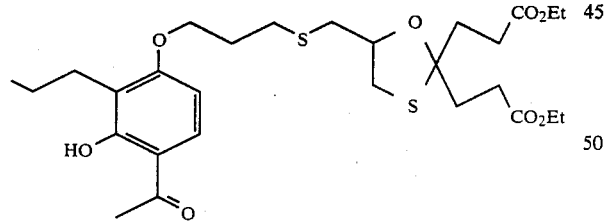

The title compound was prepared according to the procedure of Example 2 using the mercaptan produced in Example 64 (1.0 g, 0.003 mol), (3-(2-n-propyl-3-hydroxy-4-acetylphenoxy)-1-bromopropane (described in U.S. Pat. No. 4,565,882, Example 14) (1.1 g, 0.0033 mol) and anhydrous potassium carbonate (1.6 g) in methyl ethyl ketone (15 ml) The crude product was chromatographed on silica gel using 20% ethyl acetate/hexane as eluent to give 1.54 g (90%) of the product as an oil.

Analysis calculated for $C_{28}H_{42}O_8S_2$: Calc.: C, 58.93; H, 7.42; S, 10.21. Found: C, 58.68; H, 7.49; S, 9.94.

EXAMPLE 66

5-[[[3-(4-Acetyl-3-hydroxy-2-propylphenoxy)propyl]thio]methyl]-1,3-oxathiolane-2,2-dipropanoic acid

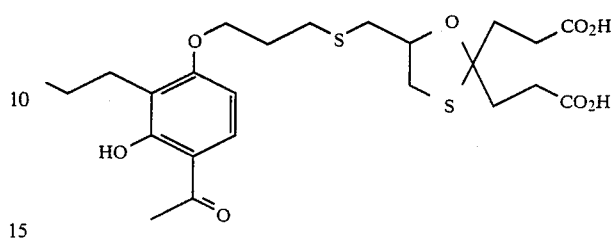

The title compound was prepared according to the procedure of Example 3 using the ester produced in Example 65 (1.3 g, 0.0023 mol) and aqueous lithium hydroxide solution (2M, 4 ml). The product, 0.923 g (78%), was obtained as an oil containing 0.33 molar equivalent of ethyl acetate.

Analysis calculated for $C_{24}H_{34}O_8S_2 \cdot \frac{1}{3}EtOAc$: Calc.: C, 55.93; H, 6.80; S, 11.76. Found: C, 55.59; H, 6.87; S, 11.88

EXAMPLE 67

Methyl 3-Benzoyl Propanoate

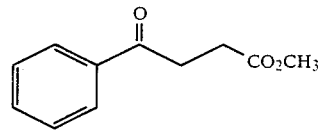

The title compound was prepared according to the procedure of Example 58 using 3-benzoylpropionic acid (20.0 g, 0.112 mol), methyl iodide (47.0 g) and sodium bicarbonate (33 g) in dimethylformamide (150 ml). The product, 19.6 g (91%) was obtained as an oil.

Analysis calculated for $C_{11}H_{12}O_3$: Calc.: C, 68.73; H, 6.30. Found: C, 68.57; H, 6.49.

EXAMPLE 68

Methyl 4-(mercaptomethyl)-2-phenyl-1,3-oxathiolane-2-propanoate

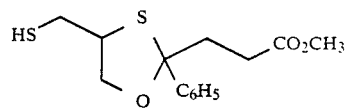

The title compound was prepared according to the procedure of Example 1 using 2,3-dimercapto-1-propanol (2.3 g, 0.019 mol), methyl 3-benzoylpropionate from Example 67 (3.7 g, 0.019 mol) and boron trifluoride etherate (0.5 ml) in methylene chloride (50 ml). The crude product was chromatographed on silica gel using 1% acetone/toluene as eluent to give 1.0 g (31%) of product.

Analysis calculated for $C_{14}H_{18}O_3S_2$: Calc.: C, 56.37; H, 6.08; S, 21.45. Found: C, 56.71; H, 6.21; S, 21.85.

EXAMPLE 69

Methyl-4-[[[3-(4-acetyl-3-hydroxy-2-propylphenoxy)propyl]thio]methyl]-2-phenyl-1,3-oxathiolane-2-propanoate

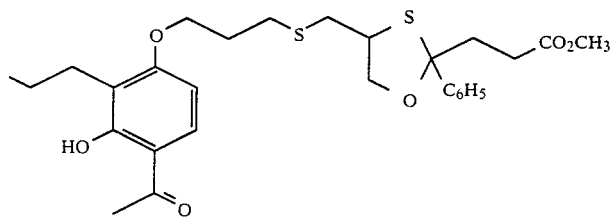

The title compound was prepared according to the procedure of Example 2 using the mercaptan produced in Example 68 (0.586 g, 0.002 mol), 3-(2-n-propyl-3-hydroxy-4-acetylphenoxy) 1-bromopropane (described in U.S. Pat. No. 4,565,882, Example 14) (0.70 g, 0.0025 mol) and anhydrous potassium carbonate (0.95 g) in methyl ethyl ketone (10 ml). The crude product was chromatographed on silica gel using 20% ethyl acetate/hexane as eluent to give 0.896 g (84%) of the product as an oil.

Analysis calculated for $C_{28}H_{36}O_6S_2$: Calc.: C, 63.14; H, 6.81; S, 12.01. Found: C, 63.01; H, 6.75; S, 11.89.

EXAMPLE 70

4-[[[3-(4-Acetyl-3-hydroxy-2-propylphenoxyl]propyl]thio]methyl]-2-phenyl-1,3-oxathiolane-2-propanoic acid

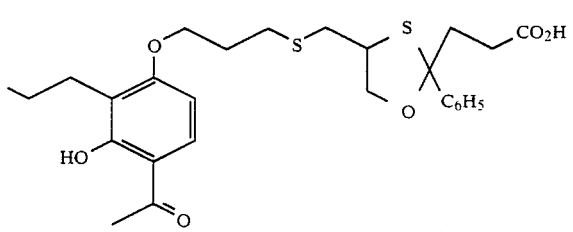

The title compound was prepared according to the procedure of Example 3 using the ester produced in Example 69 (0.75 g, 0.0014 mol) and aqueous lithium hydroxide solution (2M, 1.75 ml). The product, 0.686 g (90%), was obtained as an oil containing 0.5 molar equivalent of ethyl acetate.

Analysis calculated for $C_{27}H_{34}O_6S_2$ 0.5 EtOAc: Calc.: C, 61.91; H, 6.80; S, 11.38. Found: C, 61.96; H, 6.88; S, 11.18.

EXAMPLE 71

4-[[[3-(4-Acetyl-3-hydroxy-2-propylphenoxy)propyl]sulfinyl]methyl]2-methyl-1,3-dithiolane-2-butanoic acid

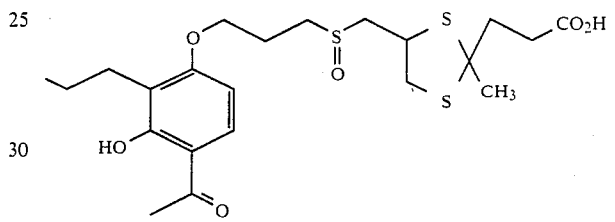

The title compound was prepared according to the procedure of Example 48 using the sulfide obtained in Example 61 (0.15 g, 0.0003 mol) and m-chloroperbenzoic acid (0.063 g, 0.0003 mol) in methylene chloride (3 ml). The crude product was chromatographed on silica gel using ethyl acetate containing 1% acetic acid to give 0.063 g (45%) of the desired product as an oil containing one molar equivalent of acetic acid.

Analysis calculated for $C_{23}H_{34}O_6S_3 \cdot CH_3CO_2H$: Calc.: C, 53.37; H, 6.80; S, 16.33. Found: C, 53.31; H, 6.81; S, 16.16.

EXAMPLE 72

4-[[[3-(4-acetyl-3-hydroxy-2-propylphenoxy]propyl]sulfinyl]methyl]-1,3-oxathiolane-2,2-dipropanoic acid

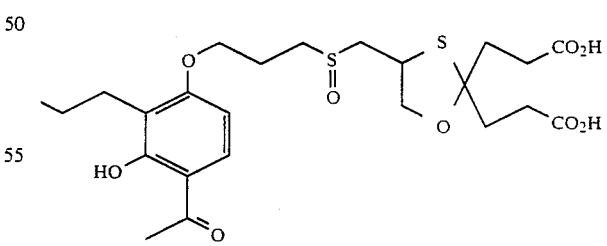

The title compound was prepared according to the procedure of Example 46 using the sulfide obtained in Example 3 (0.15 g, 0.0003 mol) and m chloroperbenzoic acid (0.062 g, 0.0003 mol) in methylene chloride (3 ml). The crude product was chromatographed on silica gel using ethyl acetate containing 0.5% acetic acid to give 0.070 g (45%) of the desired product as an oil.

Analysis calculated for $C_{24}H_{34}O_9S_2$: Calc.: C, 54.33; H, 6.46; S, 12.06. Found: C, 54.58; H, 6.41; S, 11.70.

4,923,891

EXAMPLE 73

Methyl 4-oxobutanoate

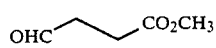

The title compound was prepared by hydrogenation of 3-carbomethoxypropionyl chloride (25.0 g, 0.166 mol) in tetrahydrofuran (250 ml) containing 2,6-dimethylpyridine (1 eq) using 10% Pd/C (2.5 g) as catalyst at 5 psi. The reaction mixture was filtered and the solvent removed using the rotary evaporator. The residual oil was distilled to give 14.5 g (79%), b. p. 63°–65° (10 mm Hg).

Analysis calculated for $C_5H_8O_3$: Calc.: C, 51.72; H, 6.89. Found: C, 51.89; H, 7.15.

EXAMPLE 74

Methyl 4-(mercaptomethyl)-1,3-dithiolane-2-propanoate

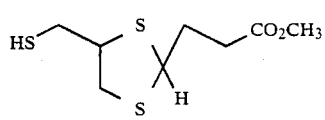

The title compound was prepared according to the procedure of Example 1 using 1,2,3-trimercaptopropane (4.21 g, 0.03 mol), methyl 4-oxobutanoate from Example 73 (3.5 g, 0.03 mol) and boron trifluoride etherate (1 ml) in methylene chloride (75 ml). The crude product was chromatographed on silica gel using 5% ethyl acetate/hexane as eluent to give 2.5 g (35%) of product.

Analysis calculated for $C_8H_{12}O_2S_3$: Calc.: C, 40.34; H, 5.92; S, 40.30. Found: C, 40.01; H, 6.10; S, 40.61.

EXAMPLE 75

Methyl 4-[[[3-(4-acetyl-3-hydroxy-2-propylphenoxy)propyl]thio]methyl]-1,3-dithiolane-2-propanoate

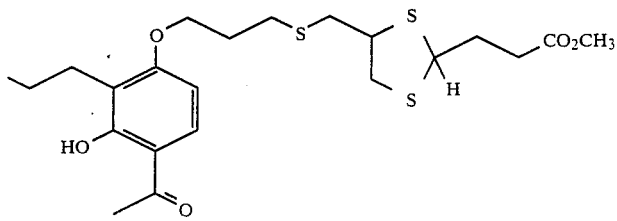

The title compound was prepared according to the procedure of Example 2 using the mercaptan produced in Example 74 (1.0 g, 0.004 mol), 3-(2-n-propyl-3-hydroxy-4-acetylphenoxy)-1-bromopropane (described in U.S. Pat. No. 4,565,882, Example 14) (1.4 g, 0.004 mol) and anhydrous potassium carbonate (2.0 g). The crude product was chromatographed on silica gel using 15% ethyl acetate/hexane as eluent to give 1.60 g (81%) of the product as an oil.

Analysis calculated for $C_{22}H_{32}O_5S_3$: Calc.: C, 55.92; H, 6.82; S, 20.31. Found: C, 55.87; H, 6.78; S, 20.02.

EXAMPLE 76

4-[[[3-(4-Acetyl-3-hydroxy-2-propylphenoxy)-propyl]thio]

methyl]-1,3-dithiolane-2-propanoic acid

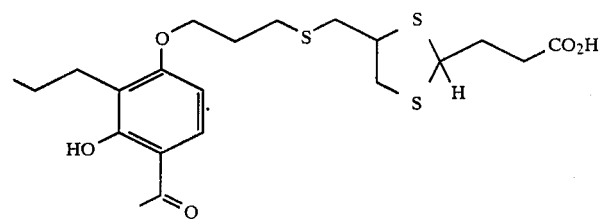

The title compound was prepared according to the procedure of Example 3 using the ester produced in Example 75 (1.30 g, 0.00275 mol) and aqueous lithium hydroxide solution (2M, 3.5 ml). The product, 1 06 g (85%), was obtained as an oil containing 0.33 molar equivalent of ethyl acetate.

Analysis calculated for $C_{21}H_{30}O_5S_3$ 0.33 EtOAc: Calc.: C, 54.98; H, 6.75; S, 19.67. Found: C, 55.30; H, 6.58; S, 19.26.

EXAMPLE 77

Methyl 4-[[[3-(4-acetyl-3-hydroxy-2-propylphenoxy)-2-hydroxypropyl]thio]methyl]-2-methyl-1,3-dithiolane-2-butanoate

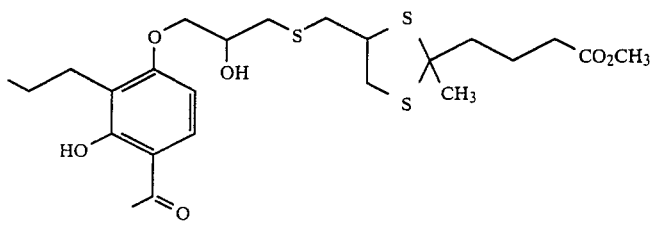

The title compound was prepared according to the procedure of Example 2 using the mercaptan produced in Example 59 (1.12 g, 0.00425 mol), 3-(2-n-propyl-3-hydroxy-4-acetylphenoxy)-1,2-epoxypropane (described in U.S. Pat. No. 4,565,882, Example 18) (1.05 g, 0.00425 mol) and anhydrous potassium carbonate (1.5 g). The crude product was chromatographed on silica gel using 25% ethyl acetate/hexane as eluent to give 2.10 g (96%) of the product as an oil.

Analysis calculated for $C_{24}H_{36}O_6S_3$: Calc.: C, 55.80; H, 7.02; S, 18.73. Found: C, 55.73; H, 7.15; S, 18.64.

EXAMPLE 78

4-[[[3-(4-Acetyl-3-hydroxy-2-propylphenoxy)-2-hydroxypropyl]thio]methyl]-2-methyl-1,3-dithiolane-2-butanoic acid

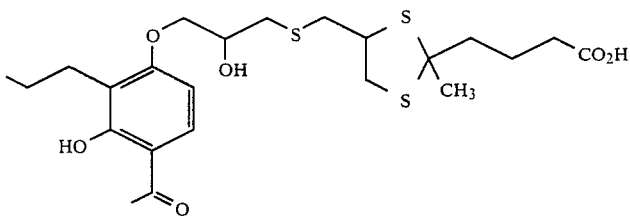

The title compound was prepared according to the procedure of Example 3 using the ester produced in Example 77 (1.75 g, 0.0034 mol) and aqueous lithium hydroxide solution (2M, 6 ml). The product, 1.55 g (91%), was obtained as an oil containing 0.33 molar equivalent of ethyl ether.

Analysis calculated for $C_{23}H_{34}O_6S.0.33\ C_4H_{10}O$: Calc.: C, 55.43; H, 7.13; S, 18.21. Found: C, 55.55; H, 7.05; S, 17.86.

EXAMPLE 79

3-(2-n-Propyl-3-methoxy-4-acetylphenoxy)-1-bromopropane

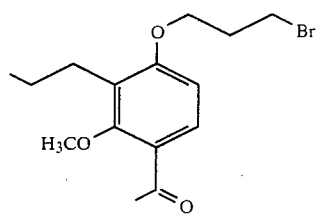

3.15 g (0.01 mole) of 3-(2-n-propyl-3-hydroxy-4-acetylphenoxy)1-bromopropane was dissolved in 50 ml of dry acetone. To this solution was added 2.75 g (0.02 mole) of anhydrous potassium carbonate and 3 g (0.02 mole) of methyl iodide. After refluxing for four days under an argon atmosphere, the reaction mixture was filtered and the filtrate concentrated on the rotary evaporator. The residue was chromatographed on silica gel eluting with 2% ethyl acetate/toluene to give 3.1 g (94%) of the title compound as an oil.

Analysis calculated for $C_{15}H_{21}O_3Br$: Calc.: C, 54.70; H, 6.43; Br, 24.29. Found: C, 54.65; H, 6.57; Br, 24.03.

EXAMPLE 80

Methyl 4-[[[3-(4-acetyl-3-methoxy-2-propylphenoxy)propyl]thio]methyl]-2-methyl-1,3-dithiolane-2-butanoate

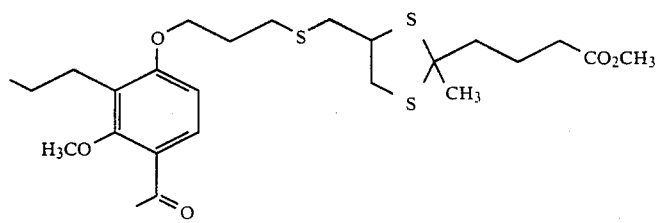

1.24 g (0.0037 mole) of bromide described in Example 79 was dissolved in 15 ml of methyl ethyl ketone containing 1 g (0.0037 mole) of material described in Example 59. To this solution was added 1 g (7.24 mmol) of anhydrous potassium carbonate and the mixture was refluxed 14 hrs. under an argon atmosphere. The reaction was cooled and filtered and the filtrate was evaporated. The residue was chromatographed on silica gel using 4% ethyl acetate/ toluene as eluent to give 1.8 g (95%) of product as an oil.

Analysis calculated for $C_{25}H_{38}O_5S_3$: Calc.: C, 58.35; H, 7.44; S, 18.65. Found: C, 58.28; H, 7.56; S, 18.51.

EXAMPLE 81

4-[[[3-(4-Acetyl-3-methoxy-2-propylphenoxy)propyl]-thio]methyl]-2-methyl-1,3-dithiolane-2-butanoic acid

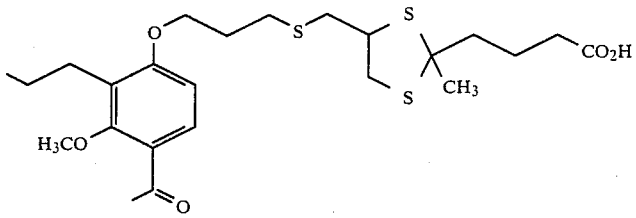

1.8 g (0.035 mole) of compound described in Example 80 was dissolved in 30 ml of methanol. To this mixture was added 5 ml of aqueous 2M lithium hydroxide solution. The mixture was stirred at room temperature for 4 hrs. and warmed to 40° C. for 1 hr. The reaction mixture was concentrated on the rotary evaporator and the residue dissolved in water. This was acidified to pH 3.5 using 0.5N $KHSO_4$ and extracted with ethyl acetate. The organic layer was washed with saturated aqueous sodium chloride solution and dried over sodium sulfate. The drying agent was filtered and the filtrate concentrated on the rotary evaporator to give a viscous oil. The oil was further dried at 100° C. (0.05 mm Hg) for 3 hrs. to give 1.56 g (89%) of the title compound as an oil.

Analysis calculated for $C_{24}H_{36}O_5S_3$: Calc.: C, 57.58; H, 7.25; S, 19.17. Found: C, 57.20; H, 7.38; S, 19.14.

EXAMPLE 82

Methyl 4-(mercaptomethyl)-2-methyl-1,3-oxathiolane-2-butanoate

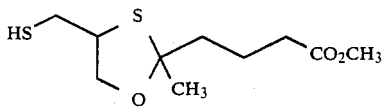

The title compound was prepared according to the procedure of Example 1 using 2,3-dimercaptopropanol (2.8 g, 0.022 mol), methyl 4-acetylbutyrate (3.2 g, 0.022 mol) and boron trifluoride etherate (0.62 ml) in methylene chloride (70 ml). The crude product was chromatographed on silica gel using 10% ethyl acetate/hexane as eluent to give 0.91 g (16.5%) of product.

Analysis calculated for $C_{10}H_{18}O_3S_2$: Calc.: C, 47.99; H, 7.25; S, 25.57. Found: C, 48.07; H, 7.31; S, 25.74.

EXAMPLE 83

Methyl 4-[[[3-(4-acetyl-3-hydroxy-2-propylphenoxy)propyl]thio]methyl]-2-methyl 1,3-oxathiolane-2-butanoate

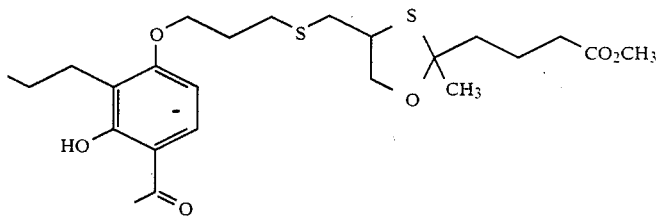

The title compound was prepared according to the procedure of Example 2 using the mercaptan produced in Example 82 (0.90 g, 0.0036 mol), 3-(2-n-propyl-3-hydroxy-4-acetylphenoxy)-1-bromopropane (described in U.S. Pat. No. 4,565,882, Example 14) (1.2 g, 0.0036 mol) and anhydrous potassium carbonate (1.5 g) in methyl ethyl ketone (15 ml). The crude product was chromatographed on silica gel using 5% ethyl acetate/hexane as eluent to give 1.3 g (75%) of the product as an oil.

Analysis calculated for $C_{24}H_{36}O_6S_2$: Calc.: C, 59.49; H, 7.49; S, 13.20. Found: C, 58.98; H, 7.30; S, 12.90.

EXAMPLE 84

4-[[[3-(4-Acetyl-3-hydroxy-2-propylphenoxy]propyl]-thio]methyl-2-methyl-1,3-oxathiolane-2-butanoic acid

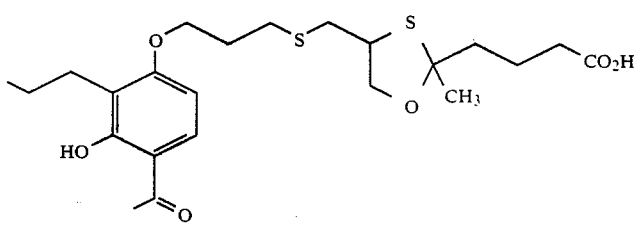

The title compound was prepared according to the procedure of Example 3 using the ester produced in Example 83 (1.05 g, 0.002 mol) and aqueous lithium hydroxide solution (2M, 2.5 ml). The product, 0.90 g (96%), was obtained as an oil.

Analysis calculated for $C_{23}H_{34}O_6S_2$: Calc.: C, 58.70; H, 7.28; S, 13.60. Found: C, 58.38; H, 7.37; S, 13.71.

EXAMPLES 85 to 94

Compounds 1 (a-d) and 2(a-d) are prepared according to the following reaction scheme.

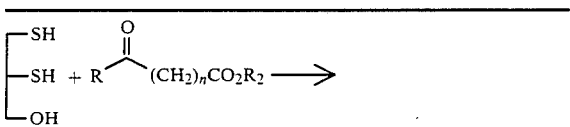

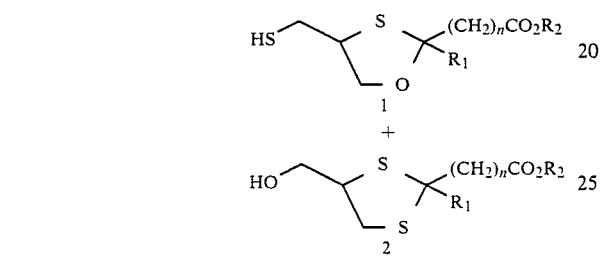

| Example No. | Compound | n | $R_1$ | $R_2$ |
|---|---|---|---|---|
| 85 | 1a | 3 | Et | Me |
| 86 | 1b | 3 | cyclohexyl | Me |
| 87 | 1c | 1 | Me | Et |
| 88 | 1d | 2 | Et | Me |

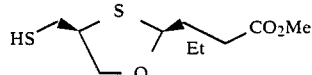

Example 89 1f(1e)

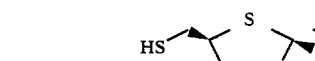

Example 90 1e(1f)

| Example No. | Compound | n | $R_1$ | $R_2$ |
|---|---|---|---|---|
| 91 | 2a | 3 | Et | Me |
| 92 | 2b | 3 | cyclohexyl | Me |
| 93 | 2c | 1 | Me | Et |
| 94 | 2d | 2 | Et | Me |

The oxa and dithiolane compounds of Examples 85 to 94 were prepared according to the following procedure.

General Procedure for the Synthesis of Oxa and Dithiolane Ring Systems 1 and 2

An equimolar ratio of the appropriate keto ester and 2,3-dimercapto-1-propanol were dissolved in benzene (0.68-1.3 mmol/ml) and a minimum amount of con. hydrochloric acid (85-300 mg) was added. The reaction was stirred at room temperature for 3-4 days. In the case of 1c, the reaction was refluxed for an additional 2 days. The reaction was poured into 5% $K_2CO_3$ solution, the layers separated and the organic layer washed once with saturated aqueous sodium chloride solution. After drying the organic layer over sodium sulfate, the drying agent was filtered and the filtrate stripped on the rotary evaporator. The residual oil was purified by chromatography on silica gel using mixtures of ethyl acetate and hexane. The oxa and dithiolanes were isolated pure.

1a: 37% yield
2a: 25% yield

Careful chromatography of 6.4 g of 1d on preparative HPLC using 2 columns of silica gel in series and 5% ethyl acetate/hexane as eluent gave 1.5 g of the slightly less polar racemate (1e) and 3.8 g of the slightly more polar racemate (1f) as oils. Racemate 1e possesses either the structure shown for Example 89 or Example 90. Racemate 1f possesses the other of these two structures.

EXAMPLES 95 to 126

Compounds 3a-f and 4a-f are prepared according to the following reaction scheme.

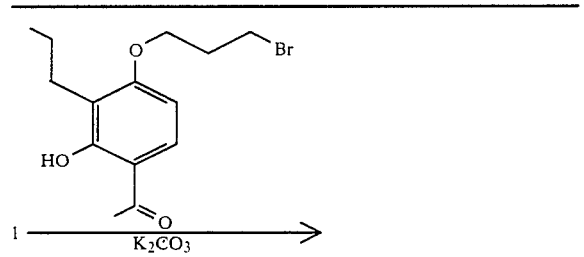

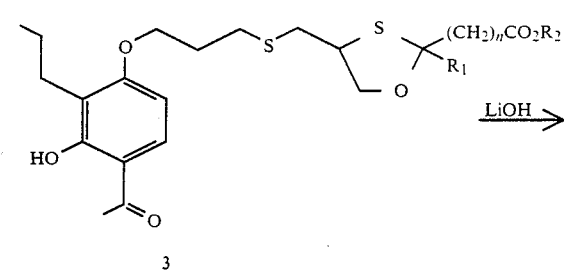

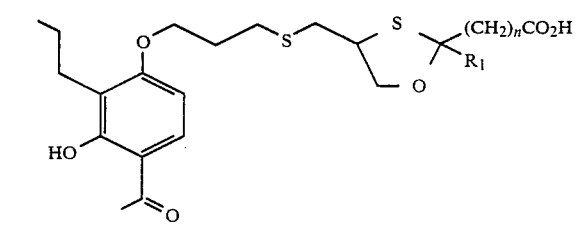

| Example No. | Compound | n | $R_1$ | $R_2$ |
|---|---|---|---|---|
| 95 | 3a | 3 | Et | Me |
| 96 | 3b | 3 | cyclohexyl | Me |
| 97 | 3c | 1 | Me | Et |
| 98 | 3d | 2 | Et | Me |
| 99 | 3e | 2 | Et | Me |
| 100 | 3f | 2 | Et | Me |
| 101 | 4a | 3 | Et | — | 4-[[[3-(4-acetyl-3-hydroxy-2-propylphenoxy)propyl]thio]methyl]-2-ethyl-1,3-oxathiolane-2-butanoic acid |
| 102 | 4b | 3 | cyclo- | — | 4-[[[3-(4-acetyl-3- |

| | | | | | -continued |
|---|---|---|---|---|---|
| | | | hexyl | | hydroxy-2-propylphenoxy) propyl]thio]methyl]-2-cyclohexyl-1,3-oxathiolane-2-butanoic acid |
| 103 | 4c | 1 | Me | — | 4-[[[3-(4-acetyl-3-hydroxy-2-propylphenoxy) propyl]thio]methyl]-2-methyl-1,3-oxathiolane-2-acetic acid |
| 104 | 4d | 2 | Et | — | 4-[[[3-(4-acetyl-3-hydroxy-2-propylphenoxy) propyl]thio]methyl]-2-ethyl-1,3-oxathiolane-2-propanoic acid |
| 105 | 4e | 2 | Et | — | (±)trans(or cis)-4-[[[3- |

| | | | | | -continued |
|---|---|---|---|---|---|
| | | | | | (4-acetyl- 3-hydroxy-2-propylphenoxy) propyl]thio]methyl]-2-ethyl-1,3-oxathiolane-2-propanoic acid |
| 106 | 4f | 2 | Et | — | (±)cis(or trans)-4-[[[3-(4-acetyl-3- hydroxy-2-propylphenoxy) propyl]thio]methyl]-2-ethyl-1,3-oxathiolane-2-propanoic acid |

3e and 3f are stereoisomers
4e and 4f are stereoisomers

Compounds 5 (a-d), 6 (a-d), 7 (a-d), 8 (a-d), and 9 (a-d) were prepared according to the following reaction scheme.

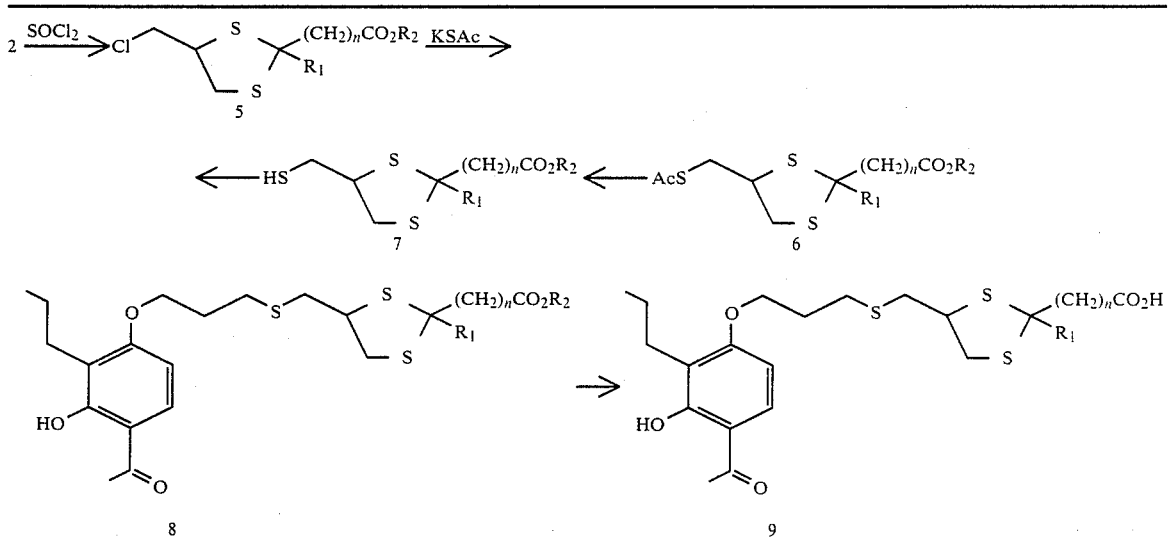

| Example No. | Compound | n | $R_1$ | $R_2$ | |
|---|---|---|---|---|---|
| 107 | 5a | 3 | Et | Me | |
| 108 | 5b | 1 | Me | Et | |
| 109 | 5c | 2 | Et | Me | |
| 110 | 5d | 2 | Et | Me | |
| 111 | 6a | 3 | Et | Me | |
| 112 | 6b | 1 | Me | Et | |
| 113 | 6c | 2 | Et | Me | |
| 114 | 6d | 2 | Et | Me | |
| 115 | 7a | 3 | Et | Me | |
| 116 | 7b | 1 | Me | Et | |
| 117 | 7c | 2 | Et | Me | |
| 118 | 7d | 2 | Et | Me | |
| 119 | 8a | 3 | Et | Me | |
| 120 | 8b | 1 | Me | Et | |
| 121 | 8c | 2 | Et | Me | |
| 122 | 8d | 2 | Et | Me | |
| 123 | 9a | 3 | Et | — | 4-[[[-(4-acetyl-3-hydroxy-2-propylphenoxy) propyl]methyl]-2-ethyl-1,3-dithiolane-2-butanoic acid |
| 124 | 9b | 1 | Me | — | 4-[[[-(4-acetyl-3-hydroxy-2-propylphenoxy) propyl]methyl]-2-methyl-1,3-dithiolane-2-acetic acid |
| 125 | 9c | 2 | Et | — | (±)trans(or cis)-4-[[[3-(4-acetyl- 3-hydroxy-2-propylphenoxy) propyl]thio] methyl]-2- ethyl-1,3-dithiolane-2- propanoic acid |
| 126 | 9d | 2 | Et | — | (±)cis(or trans)-4-[[[3-(4-acetyl- 3-hydroxy-2-propylphenoxy) propyl]thiol |

|  |  |
|---|---|
|  | methyl]-2- ethyl-1,3- dithiolane-2- propanoic acid |

5c and 5d are stereoisomers
6c and 6d are stereoisomers
7c and 7d are stereoisomers
8c and 8d are stereoisomers The compounds of Example 95 to 100 (3a–3f) and 119 to 122 (8a–8d) were prepared according to the following procedure.

General Procedure for Attachment of Sidechain to 1 and 7 to Give Compounds 3a-f and 8a-d To an equimolar solution of the mercaptan (1a-f and 7a-d) and the same bromide used in Example 2 in methyl ethyl ketone (0.16–0.40 mmol/ml) was added potassium carbonate (2.5 molar equivalents) and the reaction mixture was refluxed with stirring under a nitrogen atmosphere for 6–15 hrs. The reaction was filtered and the filtrate stripped on the rotary evaporator. The residual oil was purified by chromatography on silica gel using mixtures of ethyl acetate and hexane as eluents.

3a: 89% yield; Anal. Calcd. for $C_{25}H_{38}O_6S_2$: C, 60.02; H, 7.68; S, 12.83. Found: C, 59.84; H, 7.75; S, 12.39.

3b: 92% yield: Anal. Calcd. for $C_{29}H_{44}O_6S_2$: C, 63.02; H, 8.02; S, 11.58. Found: C, 62.61; H, 8.06; S, 11.12.

3c: 92% yield

3d: 60% yield; Anal. Calcd. for $C_{24}H_{36}O_6S_2$ C, 59.49; H, 7.48; S, 13.20. Found: C, 59.21; H, 7.63; S, 13.21.

3e: 80% yield

3f: 65% yield

8a: 95% yield; Anal. Calcd. for $C_{25}H_{38}O_5S_3$: C, 58.35; H, 7.44; S, 18.65. Found: C, 57.80; H, 7.64; S, 18.21.

8b: 60% yield; Anal. Calcd. for $C_{23}H_{34}O_5S_3$: C, 56.78; H, 7.04; S, 19.73. Found: C, 56.60; H, 7.21; S, 19.67.

8c: 92% yield

8d: 95% yield

The compounds of Examples 101 to 106 (4a-4f) and 123 to 126 (9a-9d) were prepared according to the following procedure.

General Procedure for Saponification to Target Acids 4a-f and 9a-d

To a solution of pure ester 3 or 8 in the alcohol of the ester radical (ethanol or methanol) (0.07–0.19 mmol/ml) was added aqueous 2M lithium hydroxide solution (2.5 eq). After stirring at room temperature under $N_2$ for 15–24 hrs, the reaction mixture was concentrated on the rotary evaporator, diluted with water, and acidified to pH 2.5 with 0.5N $KHSO_4$. The aqueous mixture was extracted with ethyl acetate and the organic layer dried over $MgSO_4$. The drying agent was filtered and the filtrate concentrated on the rotary evaporator to give an oil. The oil was dried on the oil pump at 65°–75° for 4–6 hrs to give the target acid.

Compounds 4e and 4f were purified by chromatography on silica gel using 30% ethyl acetate/hexane containing 0.5% HOAc as eluent. The chromatographed material was evaporated twice with methanol and dried 4 hrs at 70° under vacuum (0.1 mm Hg).

4a: 88% yield; NMR (ppm in $CDCl_3$ solution): 1.0, multiplet, 6H (2 C-$CH_3$); 2.56, s, 3H (acetyl); 3.56–3.68, multiplet, IH (ring hydrogen); 7.60, 1H, d, J=10 Hz (aromatic H); 6.44, 1H, d, J=10 Hz (aromatic H). Anal. Calcd. for $C_{24}H_{36}O_6S_2$; C, 59.50; H, 7.49; S, 13.12. Found: C, 59.28; H, 7.58; S, 12.76.

4b: 89% yield; NMR ppm in $CDCl_3$ solution):0.94, t, J=7 Hz, 3H ($CH_3$); 2.56, s, 3H (acetyl); 3.50–3.60, mult., 1H (ring hydrogen); 3.92–4.0, mult., 1H (ring hydrogen); 4.18–4.22, mult., IH (ring hydrogen); 6.44, 1H, d, J=10 Hz (aromatic H); 7.60, IH, d, J=10 Hz (aromatic H); 12.74, IH, s (phenol H). Anal. Calcd. for $C_{28}H_{42}O_6S_2$: C, 62.43; H, 7.86; S, 11.88. Found: C, 62.81; H, 7.93; S, 12.06.

4c: 89% yield; NMR (ppm in $CDCl_3$ solution): 0.94, t, J=7 Hz, 3H ($CH_3$); 1.62, 3H, s (ring methyl of one diastereomeric racemate); 1.72, 3H, s (ring methyl of other diastereomeric racemate); 2.56, 3H, s (acetyl); 3.62–3.72, 1H, mult. (H on C-2); 6.44, 1H, d, J=10 Hz (aromatic H); 7.60, IH, d, J=10 Hz (aromatic H); 12.74, 1H, s (phenol H). Anal. Calcd. for $C_{21}H_{30}O_6S_2$: C, 57.00; H, 6.83; S, 14.46. Found: C, 56.90; H, 6.88; S, 14.76.

4d: 91% yield; NMR (ppm in $CDCl_3$ solution): 0.90–1.00, 6H, mult. (two C-$CH_3$'s); 2.56, 3H, s (acetyl); 3.56–3.70, 1H, mult. (ring H); 4.03, IH, d of d, J=4 and 5 Hz (ring H); 4.20, 2H, d of d, J=4 and 5 Hz (ring H); 6.44, 1H, d, J=10 Hz (aromatic H); 7.60 (1H, d, J=10 Hz (aromatic H); 12.74, IH, s (phenol H). Anal. Calcd. for $C_{23}H_{34}O_6S_2$: C, 58.71; H, 7.28; S, 13.60. Found: C, 58.72; H, 7.40; S, 13.79. 4e: 93% yield; NMR (ppm in $CDCl_3$ solution): 0.90–1.00, 6H, mult., (overlapping signals for two C-$CH_3$'s); 4.06–4.18, 4H, mult. (two ring H and —$OCH_2$—); remaining signals are identical to 4d. Anal. Calcd. for $C_{23}H_{34}O_6S_2$: C, 58.71; H, 7.28; S, 13.60. Found: C, 58.46; H, 7.27; S, 13.51.

4f: 94% yield; NMR (ppm in $CDCl_3$ solution): 0.95, 3H, t, J=7 Hz (C-$CH_3$); 0.99, 3H, t, J=7 Hz (C-$CH_3$); remaining signals are identical to 4d. Anal. Calcd. for $C_{23}H_{34}O_6S_2$: C, 58.71; H, 7.28; S, 13.60. Found: 58.48; H, 7.36; S, 13.71.

9a: 97% yield; NMR (ppm in $CDCl_3$ solution): 0.94, 3H, t, J=7 Hz (C-$CH_3$); 1.04, 3H, t, J=7 Hz ($CH_3$ on ethyl group); 2.56, 3H, t, 7 Hz (acetyl); 3.20–3.38, 2H, mult. (ring H); 3.82–3.91, IH, mult. (ring H); 6.44, IH, d, J=10 Hz (aromatic H); 7.60, 1H, d, J=10 Hz (aromatic H); 12.74, IH, singlet (phenol). Anal. Calcd. for $C_{24}H_{36}O_5S_3$: C, 57.58; H, 7.25; S, 19.17. Found: C, 57.24; H, 7.25; S, 19.17.

9b: 89% yield; NMR (ppm in $CDCl_3$ solution): 0.94, 3H, t, J=7 Hz (C-$CH_3$); 1.90, 3H, s (ring $CH_3$ from one diastereomer); 1.95, 3H, s (ring $CH_3$ from other diastereomer ; 2.56, 3H, s (acetyl); 3.88–4.20, IH, mult. (ring H); 6.44, 1H, d, J=10 Hz (aromatic H); 7.60, 1H, d, J=10 Hz (aromatic H); 12.74, IH, s (phenol H). Anal. Calcd. for $C_{21}H_{30}O_5S_3$; C, 55.01; H, 6.60; S, 20.94. Found: C, 54.96; H.6.65; S, 20.96.

9c: 91% yield; NMR (ppm in $CDCl_3$ solution): 0.94, 3H, t, J=7 Hz (C-$CH_3$);1.06, 3H, t, J=7 Hz ($CH_3$ of ethyl group); 2.54, 3H, s (acetyl); 3.84–3.92, 1H, mult. (ring H); 6.44, 1H, d, J=10 Hz (aromatic H); 7.58, IH, d, J=10 Hz (aromatic H); 12.74, 1H, s (phenol H). Anal. Calcd. for $C_{23}H_{34}O_5S_3$: C, 56.77; H, 7.04; S, 19.73. Found: C, 56.58; H, 7.14; S, 19.48.

9d: 82% yield; NMR (ppm in CDCl$_3$ solution): 0.94, 3H, t, J=7 Hz (C-CH$_3$);1.06, 3H, t, J=7 Hz (CH$_3$ of ethyl group); 2.54, 3H, s (acetyl); 3.84–3.92, 1H, mult. (ring H); 6.44, 1H, d, J=10 Hz (aromatic H); 7.58, IH, d, J=10 Hz (aromatic H); 12.74, 1H, s (phenol H). Anal. Calcd. for C$_{23}$H$_{34}$O$_5$S$_3$: C, 56.77; H, 7.04; S, 19.73. Found: C, 56.67; H, 7.04; S, 19.85.

General Procedure For the Conversion of Alcohols 2a-d to Chlorides 5a-d

To a solution of the alcohol in benzene (0.6–0.7 mmol/ml) was added one molar equivalent of thionyl chloride. The reaction mixture was refluxed with stirring for 1 hr. The reaction was worked up by either Workup A or Workup B.

Workup A: The reaction mixture was poured onto dilute NaHCO$_3$ solution, and the layers separated. The organic layer was washed saturated NaCl solution and dried over Na$_2$SO$_4$.

The drying agent was filtered and the filtrate concentrated on the rotary evaporator. The residual oil was chromatographed on silica gel using mixtures of ethyl acetate and hexane as eluents. The pure product was obtained as an oil.

Workup B: The reaction mixture was stripped on the rotary evaporator and the residue chromatographed on silica gel using mixtures of ethyl acetate and hexane as eluents. The pure product was obtained as an oil.

5a: Workup B; 97% yield
5b: Workup A; 76% yield

The product of the reaction of dithiolane 2d (8.9 g, 35.5 mmol) with thionyl chloride (4.7 g) obtained according to Workup A was carefully chromatographed on silica gel using 5% ethyl acetate/hexane to give 1.7 g (17.9%) of a slightly less polar racemate (5c) and 1.4 g (14.7%) of a slightly more Polar racemate (5d). There was also obtained 4.5 g of an overlap fraction (total yield 80%).

The compounds of Examples 111 to 114 (6a–6d) were prepared according to the following procedure.

General Procedure for the Synthesis of Thioacetates 6a-d From Chlorides 5a-d To a stirred solution of chloride 5 in dimethylformamide (0.3–0.5 mmol/ml) was added 3–3.5 molar equivalents of potassium thioacetate. The reaction mixture was stirred 2–3 days at room temperature under a nitrogen atmosphere. The reaction mixture was poured onto water and extracted with ethyl acetate. The organic layer was washed with saturated sodium chloride solution and dried over sodium sulfate. The drying agent was filtered and the filtrate stripped on the rotary evaporator to give the oily crude product. The crude product was chromatographed on silica gel using mixtures of ethyl acetate and hexane as eluents to give the pure product as an oil.

6a: 75% yield
6b: 63% yield
6c: 87% yield
6d: 75% yield

The compounds of Examples 115 to 118 (7a–7d) were prepared according to the following procedure.

General Procedure for the Synthesis of Mercaptans 7a-d From Thioacetates 6a-d The sodium alkoxide solution was prepared from 1.2 molar equivalents of sodium metal (based on the amount of thioacetate) and the alcohol corresponding to the ester radical of 6 (ethanol or methanol). Thioacetate 6 was added (final concentration of 6 was 0.20–0.37 mmol/ml) and the reaction was stirred at room temperature under N$_2$ for 1–2 hrs. The reaction was poured into 0.5N KHSO$_4$, extracted with ethyl acetate and dried over Na$_2$SO$_4$. The drying agent was filtered, the filtrate concentrated in vacuo and the residue chromatographed on silica gel using mixtures of ethyl acetate and hexane as eluents to give the pure mercaptan 7 as an oil.

7a: 92% yield
7b: 63% yield
7c: 89% yield
7d: 84% yield

EXAMPLE 127

4-[[[3-(4-acetyl-3-hydroxy-2-propylphenoxy)propyl]thio]methyl]-2-methyl-1,3-dithiolane-2-butanoic acid, sodium salt

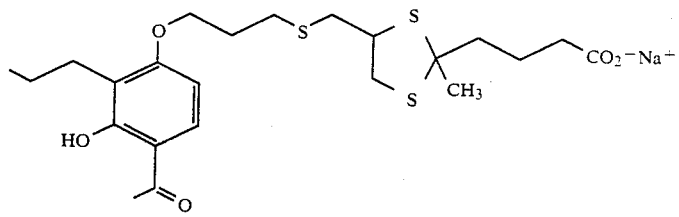

To a stirred solution of the product of Example 61 (458 mg, 0.94 mmol) in methanol (10 ml) was added 1.00 ml of 0.996N NaOH solution. After stirring the reaction at room temperature for 1 hr., solvent was removed using the rotary evaporator and the residue was evaporated three times with methanol and once with benzene. The resulting product was a glass.

Anal. Calcd. for C$_{23}$H$_{33}$O$_5$S$_3$Na: C, 54.32; H 6.54; S, 18.88. Found: C, 53.87; H, 6.46; S, 19.32.

EXAMPLE 128

(a) Methyl 4-(mercaptomethyl)-2-ethyl-1,3-oxathiolane-2-propanoate

To a solution of methyl 4-oxohexanoate (10 g, 0.069 mol) and 2,3-dimercapto-1-propanol (9 g, 0.072 mol) in benzene (120 ml) was added con. hydrochloric acid (1 ml). The reaction mixture was stirred at room temperature under N$_2$ for 3 days. The reaction mixture was diluted with ethyl acetate (200 ml) and washed with 5% aqueous K₂CO₃ (twice with 100 ml portions). After washing with saturated aqueous NaCl, the organic layer was dried over Na₂SO₄.

The drying agent was filtered and the filtrate chromatographed on silica gel (Waters PrepPak concentrated in vacuo. The residual oil was 500/Silica) using 15% ethyl acetate/hexane to give 6.4 g (37%) of the title compound and 4.0 g (23%) of methyl 4-(hydroxymethyl)-2-ethyl-1,3-dithiolane-2-propanoate.

Oxathiolane NMR δ (ppm): 0.9–1.05, t, J=6 Hz (CH₂CH₃); 1.60, t, J=9.8 Hz and 1.62, t, J=9.8 Hz, 1H (SH); 1.80–1.90, 2H, mult. (CH₂CH₃); 3.68, 3H, s (OCH₃).

(b) Methyl 4-[[[3-(4-acetyl-3-hydroxy-2-propylphenoxy)propyl]thio]methyl]-2-ethyl-1,3-oxathiolane-2-propanoate (compound 3d)

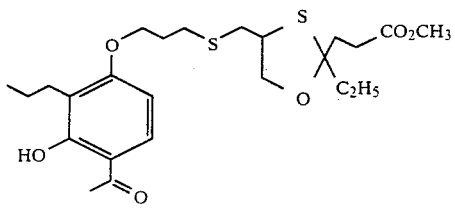

A mixture of K₂CO₃ (10 g) and a solution of the mercaptan prepared in part (a) (6.4 g, 0.0255 mol) and the same bromide used in Example 2 (8.0 g, 0.0255 mol) in methyl ethyl ketone (100 ml) was refluxed with stirring under N₂ for 12 hrs.

The reaction was cooled and filtered. The filtrate was concentrated in vacuo and the oily residue chromatographed on silica gel (Waters PrepPak 500) using 20% ethyl acetate/hexane to give 12 g (97% yield) of the titled compound. NMR δ (PPm): 1.52, 2H, sextet, J=6 Hz (CH₂CH₂CH₃); 1.80–1.92, 2H, mult. (methylene of ethyl group); 3.68, 3H, singlet (OCH₃); 6.46, 1H, d and 7.60, 1H, d (aromatic H); 12.75, 1H, singlet (phenol).

Anal. Calcd. for C₂₄H₃₆O₆S₂: C, 59.49; H, 7.48; S, 13.20.

Found: C, 59.41; H, 7.63; S, 13.21.

(c) 4-[[[3-(4-acetyl-3-hydroxy-2-propylphenoxy)propyl]thio]methyl]-2-ethyl-1,3-oxathiolane-2-propanoic acid (compound 4d)

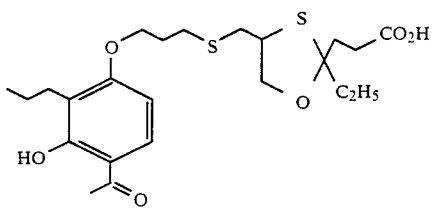

The ester prepared in part b) (7.0 g, 0.0144 mol) was stirred overnight at room temperature under N₂ with aqueous LiOH solution (2M, 20 ml) in methanol (100 ml).

The reaction was concentrated on the rotary evaporator and the residue diluted with water. The resulting solution was washed once with ethyl ether and then acidified to pH 2.5 with 0.5N KHSO₄ solution. The aqueous mixture was extracted with ethyl acetate and the organic layer dried over MgSO₄.

The drying agent was filtered and the filtrate concentrated on the rotary evaporator to give an oily residue which was purified by chromatography on silica gel (Waters PrepPak 500) using 30% ethyl acetate/hexane containing 0.5% acetic acid. The isolated product was azeotroped three times with methanol and once with benzene to remove acetic acid. After drying under vacuum on the oil pump at 60° for 3 hrs., there was obtained 6.27 g (92% yield) of titled product as an oil. NMR δ (ppm): 1.51, 2H, doublet, J = 7 Hz (middle methylene of propyl group); 2.58, 3H, singlet (acetyl methyl); 2.63, 2H, triplet, J=7 Hz (ArCH₂CH₂—); 6.44, 1H, d and 7.60, 1H, d (aromatic H); 12.72, 1H, singlet (phenol).

Anal. Calcd. for C₂₃H₃₄O₆S₂: C, 58.71; H, 7.28, S, 13.60.

Found: C, 58.62; H, 7.40, S, 13.61.

EXAMPLE 129

Methyl 4-[[[3-(4-acetyl-3-hydroxy-2-propylphenoxy)propyl]thio]methyl]-2-ethyl-1,3-oxathiolane-2-propanoate

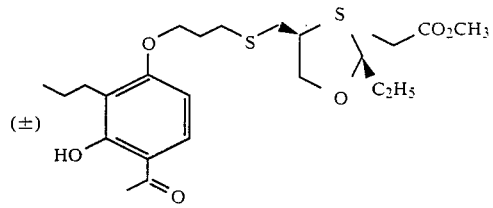

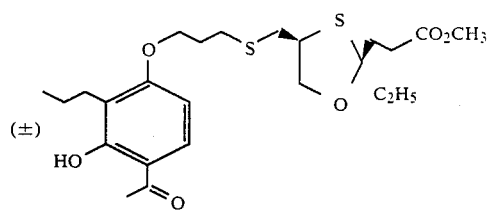

(a) Synthesis of 3e

To a solution of the less polar racemic mercaptan compound 1e (0.80 g, 0.0032M) and the same bromide used in Example 2 1.0 g, 0.0032M) in methyl ethyl ketone (20 ml) was added potassium carbonate 1.1 g) and the reaction mixture was refluxed with stirring overnight. The reaction mixture was filtered and the filtrate stripped on the rotary evaporator. The residual oil was purified by chromatography on silica gel using 20% ethyl acetate/hexane as eluents to give 1.2 g (80%) of compound 3e.

(b) Synthesis of 3f

To a solution of the more polar racemic mercaptan compound 1f (1.0 g, 0.004M) and the same bromide used in Example 2 (1.25 g, 0.004M) in methyl ethyl ketone (20 ml) was added potassium carbonate (1.4 g) and the reaction mixture was refluxed with stirring overnight. The reaction mixture was filtered and the filtrate stripped on the rotary evaporator. The residual oil was purified by chromatography on silica gel using 20% ethyl acetate/hexane as eluents to give 1.2 g (65%) of compound 3f.

EXAMPLE 130

(±) trans/cis-4-[[[3-(4-acetyl-3-hydroxy-2-propylphenoxy)-propyl]thio]methyl]-2-ethyl-1,3-oxathiolane-2-propanoic acid

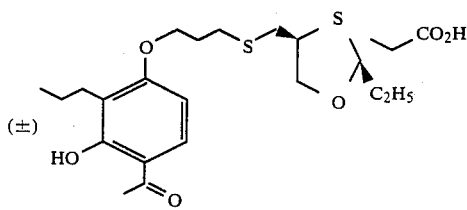

(±)

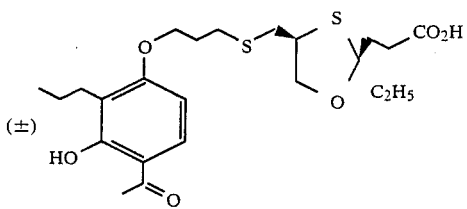

(±)

(a) Synthesis Of 4e

To a solution of compound 3e (Example 129a) (0.71 g, 0.00146M) in methanol (10 ml) was added aqueous 2M lithium hydroxide solution (2 ml). After stirring overnight at room temperature under $N_2$, the reaction mixture was concentrated on the rotary evaporator, diluted with water, and acidified to pH 2.5 with 0.5N $KHSO_4$. The aqueous mixture was extracted with ethyl acetate and the organic layer dried over $MgSO_4$. The drying agent was filtered and the filtrate concentrated on the rotary evaporator to give an oil.

The oil was purified by chromatography on silica gel using 30% ethyl acetate/hexane containing 0.5% HOAc as eluent to give 0.64 g (93%) of compound 4e. The acetic acid was removed by evaporating twice with methanol and drying 4 hrs. at 70° under vacuum (0.1 mm Hg).

NMR (ppm in $CDCl_3$ solution): 0.90–1.00, 6H, mult., (overlapping signals for two C-$CH_3$'s); 4.06–4.18, 4H, mult. (two ring H and —$OCH_2$—); remaining signals are identical to 4d.

Anal. Calcd. for $C_{23}H_{34}O_6S_2$: C, 58.71; H, 7.28; S, 13.60. Found: C, 58.46; H, 7.27; S, 13.51.

(b) Synthesis of 4f

To a solution of compound 3f (Example 129b) (0.68 g, 0.0014M) in methanol (10 ml) was added aqueous 2M lithium hydroxide solution (2 ml). After stirring overnight at room temperature under $N_2$, the reaction mixture was concentrated on the rotary evaporator, diluted with water, and acidified to pH 2.5 with 0.5N $KHSO_4$. The aqueous mixture was extracted with ethyl acetate and the organic layer dried over $MgSO_4$. The drying agent was filtered an the filtrate concentrated on the rotary evaporator to give an oil.

The oil was purified by chromatography on silica gel using 30% ethyl acetate/hexane containing 0.5% HOAc as eluent. Acetic acid was removed from the oily product by evaporating twice with methanol and drying 4 hrs. at 70° under vacuum (0.1 mm Hg) to give 0.62 g (93%) of compound 4f.

NMR (ppm in $CDCl_3$ solution): 0.95, 3H, t, J=7 Hz (C-$CH_3$); 0.99, 3H, t, J=7 Hz (C-$CH_3$; remaining signals are identical to compound 4d.

Anal. Calcd. for C, 58.71; H, 7.28; S, 13.60.
Found: C, 58,48; H, 7.36; S, 13.71.

EXAMPLE 131

(a) Synthesis of Sodium Salt of 4d 4-[[[3-(4-acetyl-3-hydroxy-2-propylphenoxy)propyl]thio]methyl]-2-ethyl-1,3-oxathiolane-2-propanoic acid, sodium salt

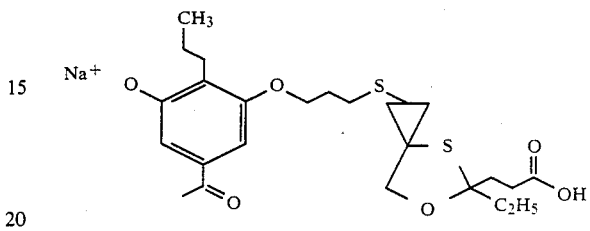

To a stirred solution of compound 4d (511 mg, 1.1 mmol) in methanol (10 ml) was added 1.12 ml of 0.996N NaOH solution. After stirring the reaction for 1 hr. at room temperature, the solvent was removed in vacuo and the residue evaporated with methanol (three times) and toluene (twice). The resulting glass was dried at 90° for 4 hrs. under vacuum (0.1 mm Hg).

Anal. Calcd. for $C_{23}H_{33}O_6S_2Na$: C, 56.08; H, 6.75; S, 12.99.
Found: C, 56.00; H, 6.65; S, 12.93.

Synthesis of the Disodium Salt of 4d

4-[[[3-(4-acetyl-3-hydroxy-2-propylphenoxy)propyl]thio]methyl]-2-ethyl-1,3-oxathiolane-2-propanoic acid, disodium salt

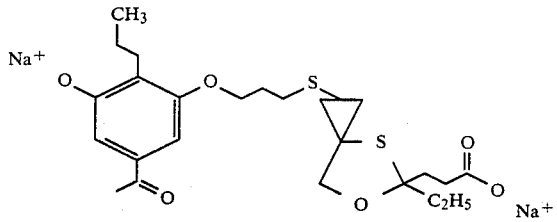

To a Stirred solution of compound 4d (470 mg, 1.0 mmol) in absolute ethanol (5 ml) was added 2 ml of 0.996N NaOH solution. After stirring the reaction for 1 hr. at room temperature, the solvent was removed in vacuo and the residue dried by azeotroping three times with benzene. The residue, which solidified upon trituration with ether, was filtered and had m.p. 125°–128°.

Anal Calcd. for $C_{23}H_{32}O_6S_2Na_2$: C, 53.69; H, 6.27; Na, 8.93; S, 12.43
Found: C, 53.22; H, 6.34; Na, 8.71; S, 12.79.

EXAMPLE 132

(a) Methyl 4-(hydroxymethyl)-2-ethyl-1,3-dioxolane-2-propanoate

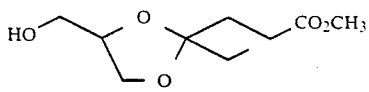

Methyl 4-oxohexanoate (14.42g, 0.1 mol), glycerol (9.21g, 0.1 mol) and p-toluenesulfonic acid (100 mg) are combined in benzene (150 ml) and refluxed with stirring for 10 hrs. using a water separator to remove water formed during the ketalization. The reaction mixture is cooled, washed successively with 5% NaOH solution and water and then dried over sodium sulfate. The drying agent is filtered and the filtrate stripped on the rotary evaporator to give the crude product. The product is purified by chromatography on silica gel using mixtures of ethyl acetate and hexane as eluents.

(b) Methyl 4-(chloromethyl)-2-ethyl-1,3-dioxolane-2-propanoate

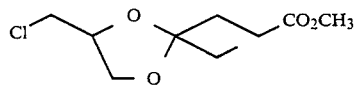

A solution of the alcohol prepared in part (a) (2.18g, 10 mmol) and thionyl chloride (1.19g, 10 mmol) in benzene (17 ml) is refluxed with stirring for 1 hr. The reaction mixture is stripped on the rotary evaporator and the residue chromatographed on silica gel using mixtures of ethyl acetate and hexane as eluents to give the chloride product.

(c) Methyl 4-[(acetylthio)methyl]-2-ethyl-1,3-dioxolane-2-propanoate

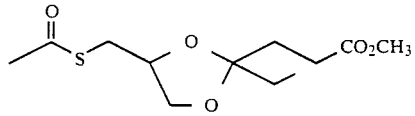

To a stirred solution of the chloride prepared in part (b) (2.37g, 10 mmol) in dimethylformamide (DMF) (20 ml) is added potassium thioacetate (3.42g, 30 mmol). The reaction mixture is stirred 2-3 days at room temperature under a nitrogen atmosphere. The reaction mixture is poured onto water and extracted with ethyl acetate. The organic layer is washed with saturated sodium chloride solution and dried over sodium sulfate. The drying agent is filtered and the filtrate stripped on the rotary evaporator to give the oily crude product. The crude product is chromatographed on silica gel using mixtures of ethyl acetate and hexane as eluents to give the thioacetate product.

(d) Methyl 4-(mercaptomethyl)-2-ethyl-1,3-dioxolane-2-propanoate

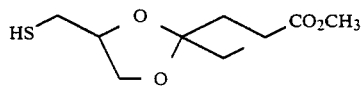

Sodium methoxide is prepared in methanol (27 ml) using sodium metal (230 mg). The thioacetate prepared in part (c) (2.52 g, 10 mmol) is added and the reaction is stirred at room temperature under a nitrogen atmosphere for 2 hrs. The reaction mixture is poured into 0.5N KHSO$_4$, extracted with ethyl acetate and dried over Na$_2$SO$_4$. The drying agent is filtered, the filtrate concentrated in vacuo and the residue chromatographed on silica gel using mixtures of ethyl acetate and hexane as eluents to give the mercaptan product.

(e) Methyl 4-[[[3-(4-acetyl-3-hydroxy-2-propylphenoxy)propyl]thio]methyl]-2-ethyl-1,3-dioxolane-2-propanoate

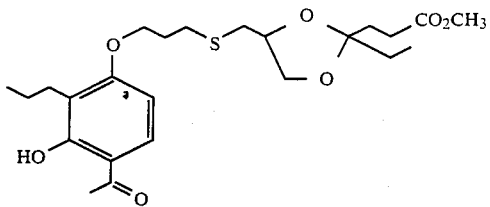

A mixture of K$_2$CO$_3$ (3.45g) in a Solution of the mercaptan prepared in part (d) (2.34 g, 10 mmol) and bromide of Example 79 (3.15 g, 10 mmol) in methyl ethyl ketone (50 ml) is refluxed with stirring under N$_2$ for 12 hrs.

The reaction is cooled and filtered. The filtrate is concentrated in vacuo and the oily residue chromatographed on silica gel using mixtures of ethyl acetate and hexane as eluents to give the product.

(f) 4-[[[3-(4-Acetyl-3-hydroxy-2-propylphenoxy)-propyl]thio]-methyl]-2-ethyl-1,3-dioxolane-2-propanoic acid

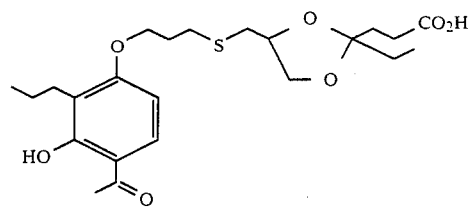

The ester prepared in part (e) (4.69 g, 10 mmol) is stirred overnight at room temperature under N$_2$ with aqueous LiOH solution (2 M, 13 ml) in methanol (60 ml). The reaction is concentrated on the rotary evaporator and the residue diluted with water. The resulting solution is washed once with ethyl ether and then acidified to pH 2.5 with 0.5N KHSO$_4$ solution. The aqueous mixture is extracted with ethyl acetate and the organic layer dried over MgSO$_4$.

The drying agent is filtered and the filtrate concentrated on the rotary evaporator to give an oily residue which is purified by chromatography on silica gel using mixtures of ethyl acetate and hexane containing 0.5% acetic acid as eluents. The purified product is evaporated with methanol and benzene to remove acetic acid. The resulting product is dried on the oil pump (0.1 mm Hg) 60° to give the acid product.

What is claimed is:

1. A compound of the formula

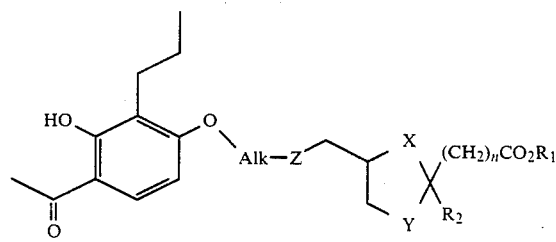

or a pharmaceutically acceptable salt or geometrical or optical isomer thereof wherein:

X is S;

Y is O or S;

Z is S;

Alk is —CH$_2$—CH$_2$—CH$_2$—;

R$_1$ is hydrogen, methyl or ethyl;

n is 1, 2, or 3; and

R$_2$ is lower alkyl or cycloalkyl.

2. A compound according to claim 1 wherein Y is O and R$_2$ is methyl, ethyl, or cyclohexyl.

3. A compound according to claim 1 wherein Y is S and R$_2$ is methyl or ethyl.

4. A compound, which is diethyl 4-[[[3-(4-acetyl-3-hydroxy-2-propylphenoxy)-2-hydroxypropyl]thio]methyl]-1,3-oxathiolane-2,2-dipropanoate and isomers thereof.

5. A compound, which is 4-[[[3-(4-acetyl-3-hydroxy-2-propylphenoxy)propyl]thio]methyl]-1,3-oxathiolane-2,2-dipropanoic acid and isomers thereof.

6. A compound, which is 4-[[[3-(4-acetyl-3-hydroxy-2-propylphenoxy)propyl]thio]methyl-2-methyl-1,3-oxathiolane-2-propanoic acid and isomers thereof.

7. A compound, according to claim 4, which is 4-[[[3-(4-acetyl-3-hydroxy-2-propylphenoxy)propyl]thio]methyl]-2-ethyl-1,3-oxathiolane-2-butanoic acid and isomers thereof.

8. A compound, according to claim 1, which is 4-[[[3-(4-acetyl-3-hydroxy-2-propylphenoxy)propyl]thio]methyl]-2-cyclohexyl-1,3-oxathiolane-2-butanoic acid and isomers thereof.

9. A compound, according to claim 1, which is 4-[[[3-(acetyl-3-hydroxy-2-propylphenoxy)propyl]thio]methyl]-2-methyl-1,3-oxathiolane-2-acetic acid and isomers thereof.

10. A compound, according to claim 1, which is 4-[[[3-(4-acetyl-3-hydroxy-2-propylphenoxy)propyl]thio]methyl]-2-ethyl-1,3-oxathiolane-2-propanoic acid and isomers thereof.

11. A compound, according to claim 1, which is (±)trans-4-[[[3-(4-acetyl-3-hydroxy-2-propylphenoxy)propyl]thio]methyl]-2-ethyl-1,3-oxathiolane-2-propanoic acid and isomers thereof.

12. A compound, according to claim 1, which is (±)cis-4-[[[-(4-acetyl-3-hydroxy-2-propylphenoxy)propyl]thio]methyl]-2-ethyl-1,3-oxathiolane-2-propanoic acid and isomers thereof.

13. A compound, according to claim 1, which is 4-[[[3-(4-acetyl-3-hydroxy-2-propylphenoxy)propyl]thio)methyl]-2-ethyl-1,3-dithiolane-2-butanoic acid and isomers thereof.

14. A compound, according to claim 1, which is 4-[[[3-(4-acetyl-3-hydroxy-2-propylphenoxy)propyl]thio]ethyl]-2-methyl-1,3-dithiolane-2-acetic acid and isomers thereof.

15. A compound, according to claim 1, which is (±)trans-4-[[[3-(4-acetyl-3-hydroxy-2-propylphenoxy)propyl]thio]methyl]-2-ethyl-1,3-dithiolane-2-propanoic acid and isomers thereof.

16. A compound, according to claim 1, which is (±)cis-4-[[[3-(4-acetyl-3-hydroxy-2-propylphenoxy)propyl]thio)methyl]-2-ethyl-1,3-dithiolane-2-propanoic acid and isomers thereof.

17. A compound according to claim 1 which is 4-[[[3-(4-acetyl-3-hydroxy-2-propylphenoxy)propyl]thio]methyl]-2methyl-1,3-dithiolane-2-butanoic acid, sodium salt and isomers thereof.

18. A compound according to claim 1 which is 4-[[[3-(4-acetyl-3-hydroxy-2-propylphenoxypropyl]thio]methyl-2-methyl-1,3-dithiolane-2-butanoic acid, sodium salt and isomers thereof.

19. A compound according to claim 1 which is 4-[[[3-(4-acetyl-3-hydroxy-2-propylphenoxy)propyl]-thio]methyl]-2-ethyl-1,3-oxathiolane-2-propanoic acid, disodium salt and isomers thereof.

20. A pharmaceutical composition comprising a therapeutically effective amount of a compound of the formula

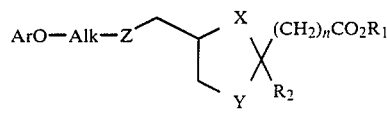

or a pharmaceutically acceptable salt or geometrical or optical isomer thereof wherein:

X, Y, and Z are each independently O or S with S optionally oxidized to S=O;

Alk is straight or branched chain alkylene or hydroxyalkylene containing 1–6 carbon atoms;

R$_1$ is hydrogen or lower alkyl;

n is 0 to 5;

R$_2$ is hydrogen, lower alkyl, cycloalkyl, —(CH$_2$)$_n$—CO$_2$R$_1$, phenyl, phenyl substituted with halo, lower alkyl or lower alkoxy; and Ar is 5,6,7,8-tetrahydro-1-naphthalenyl, phenyl, or phenyl substituted with lower alkyl, hydroxy, lower alkoxy, or lower alkanoyl;

and a pharmaceutically acceptable carrier.

21. A pharmaceutical composition according to claim 20 comprising a therapeutically effective amount of a compound of the formula

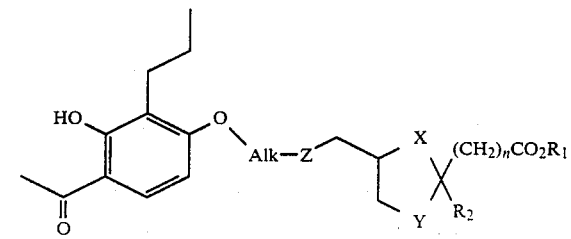

or a pharmaceutically acceptable salt or geometrical or optical isomer thereof wherein:

X, Y, and Z are each independently O or S with S optionally oxidized to S=O;

Alk is straight or branched chain alkylene or hydroxyalkylene containing 1–6 carbon atoms;

R$_1$ is hydrogen or lower alkyl;

n is 0 to 5; and

R$_2$ is hydrogen, lower alkyl, cycloalkyl, —(CH$_2$)$_n$—CO$_2$R$_1$, phenyl, phenyl substituted with halo, lower alkyl or lower alkoxy;

and a pharmaceutically acceptable carrier.

22. A pharmaceutical composition according to claim 20 comprising a therapeutically effective amount of a compound of the formula

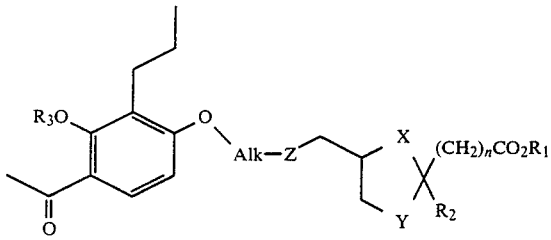

or a pharmaceutically acceptable salt or geometrical or optical isomer thereof wherein:
- X, Y, and Z are each independently O or S with S optionally oxidized to S=O;
- Alk is straight or branched chain alkylene or hydroxyalkylene containing 1-6 carbon atoms;
- $R_1$ is hydrogen or lower alkyl;
- n is 0 to 5;
- $R_2$ is hydrogen, lower alkyl, $-(CH_2)_n-CO_2R_1$, phenyl, phenyl substituted with halo, lower alkyl or lower alkoxy; and $R_3$ is lower alkyl;
and a pharmaceutically acceptable carrier.

23. A pharmaceutical composition according to claim 21 comprising a therapeutically effective amount of a compound of the formula

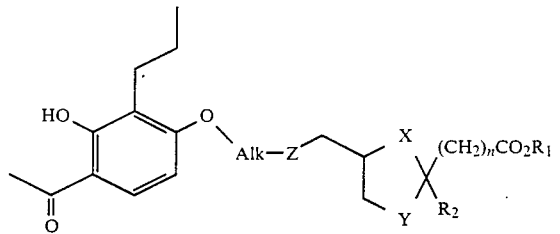

or a pharmaceutically acceptable salt or geometrical or optical isomer thereof wherein:
- X is S;
- Y is O or S;
- Z is S;
- Alk is $-CH_2-CH_2-CH_2-$;
- $R_1$ is hydrogen, methyl, or ethyl;
- n is 1, 2, or 3; and
- $R_2$ is lower alkyl or cycloalkyl;
and a pharmaceutically acceptable carrier.

24. A pharmaceutical composition according to claim 23 wherein Y is O and $R_2$ is methyl, ethyl, or cyclohexyl.

25. A pharmaceutical composition according to claim 23 wherein Y is S and $R_2$ is methyl or ethyl.

26. A pharmaceutical composition according to claim 21 wherein said compound is 4-[[[3-(4-acetyl-3-hydroxy-2-propylphenoxy]thio]methyl-2-ethyl-1,3-oxathiolane-2-propanoic acid.

27. A pharmaceutical composition according to claim 21 wherein said compound is 4-[[[3-(4-acetyl-3-hydroxy-2-propylphenoxy)propyl]thio methyl]-2-ethyl-1,3-oxathiolane-2-propanoic acid, sodium salt.

28. A pharmaceutical composition according to claim 21 wherein said compound is 4-[[[3-(4-acetyl-3-hydroxy-2-propylphenoxy)propyl]thio methyl]-2-ethyl-1,3-oxathiolane-2-propanoic acid, disodium salt.

29. A pharmaceutical composition according to claim 21 wherein said compound is (±)trans-4-[[[3-(4-acetyl-3-hydroxy-2-propylphenoxy)propyl]thio]methyl]-2-ethyl-1,3-oxathiolane-2-propanoic acid.

30. A pharmaceutical composition according to claim 21 wherein said compound is (±)cis-4-[[[3-(4-acetyl-3-hydroxy-2-propylphenoxy)propyl]thio]methyl]-2-ethyl-1,3-oxathiolane-2-propanoic acid.

31. A method of treating allergy comprising administering to an animal in need of such treatment a therapeutically effective amount of a compound of the formula

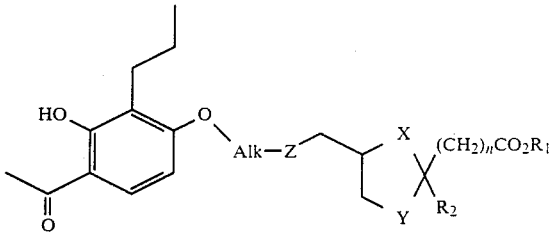

or a pharmaceutically acceptable salt or geometrical or optical isomer thereof wherein:
- X, Y, and Z are each independently O or S with S optionally oxidized to S=O;
- Alk is straight or branched chain alkylene or hydroxyalkylene containing 1-6 carbon atoms;
- $R_1$ is hydrogen or lower alkyl;
- n is 0 to 5; and
- $R_2$ is hydrogen, lower alkyl, cycloalkyl, $-(CH_2)_n-CO_2R_1$, phenyl, phenyl substituted with halo, lower alkyl or lower alkoxy.

32. A method according to claim 31 of treating allergy comprising administering to an animal in need of such treatment a therapeutically effective amount of compound of the formula

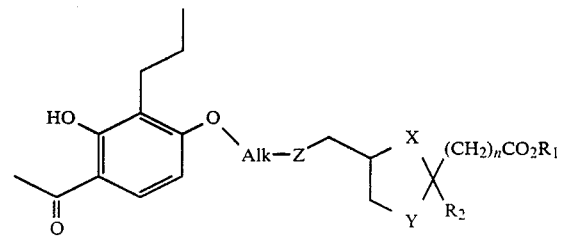

or a pharmaceutically acceptable salt or geometrical or optical isomer thereof wherein:
- X is S;
- Y is O or S;
- Z is S;
- Alk is $-CH_2-CH_2-CH_2-$;
- $R_1$ is hydrogen, methyl or ethyl;
- n is 1, 2, or 3; and
- $R_2$ is lower alkyl or cycloalkyl.

33. A method according to claim 32 wherein Y is O and $R_2$ is methyl, ethyl, or cyclohexyl.

34. A method according to claim 32 wherein Y is S and $R_2$ is methyl or ethyl.

35. A method of treating inflammatory diseases comprising administering to an animal in need of such treatment a therapeutically effective amount of compound of the formula

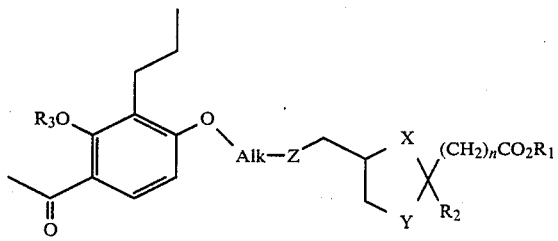

or a pharmaceutically acceptable salt or geometrical or optical isomer thereof wherein:

X, Y, and Z are each independently O or S with S optionally oxidized to S=O;

Alk is straight or branched chain alkylene or hydroxyalkylene containing 1-6 carbon atoms;

$R_1$ is hydrogen or lower alkyl;

n is 0 to 5;

$R_2$ is hydrogen, lower alkyl, $-(CH_2)_n-CO_2R_1$, phenyl, phenyl substituted with halo, lower alkyl or lower alkoxy; and $R_3$ is lower alkyl.

36. A method according to claim 31 wherein said compound is 4-[[[3-(4-acetyl-3-hydroxy-2-propylphenyl)propyl]thio]methyl]-2-ethyl-1,3-oxathiolane-2-propanoic acid.

37. A method according to claim 31 wherein said compound is 4-[[[3-(4-acetyl-3-hydroxy-2-propylphenoxy)propyl]thio]methyl]-2-ethyl-1,3-oxathiolane-2-propanoic acid, sodium salt.

38. A method according to claim 31 wherein said compound is 4-[[[3-(4-acetyl-3-hydroxy-2-propylphenoxy)propyl]thio]methyl]-2-ethyl-1,3-oxathiolane-2-propanoic acid, disodium salt.

39. A method according to claim 31 wherein said compound is (±)trans-4-[[[3-(4-acetyl-3-hydroxy-2-propylphenoxy)propyl]thio]methyl]-2-ethyl-1,3-oxathiolane-2-propanoic acid.

40. A method according to claim 31 wherein said compound is (±)cis-4-[[[3-(4-acetyl-3-hydroxy-2-propylphenoxy)propyl]thio]methyl]-2-ethyl-1,3-oxathiolane-2-propanoic acid.

* * * * *

UNITED STATES PATENT AND TRADEMARK OFFICE
CERTIFICATE OF CORRECTION

PATENT NO. : 4,923,891

DATED : May 8, 1990

INVENTOR(S) : Deason, et al.

It is certified that error appears in the above-identified patent and that said Letters Patent is hereby corrected as shown below:

Column 3, the second structure, that portion of the structure reading

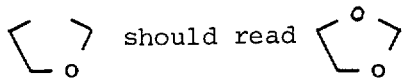 should read 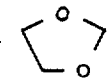

Column 5, line 59, reading "-leu phe" should read -- -leu-phe --.
Column 5, line 64, reading "X 100" should read -- X-100 --.
Column 7, line 23, reading "combinations thereof" should read -- calcium sulfate mannitol, and the like, or various combinations thereof --.
Column 8, line 37, reading "-oxathiolane" should read -- -oxathiolane- --.
Column 8, line 48, reading "dimercapto-pb 1-propanol" should read
-- dimercapto-1-propanol --.
Column 9, line 3, reading "3" should read -- 3- --.
Column 9, line 19, reading "30(2-n-Propyl-3-hydroxy-4 acetylphenoxy)-" should read -- 3-(2-n-Propyl-3-hydroxy-4-acetylphenoxy)- --.
Column 9, lines 48-49, reading "3 hydroxy-2-propylphenoxy)propyl]thio]-methyl]1,3" should read --3-hydroxy-2-propylphenoxy)propyl]thio]methyl]-1,3- --.
Column 10, line 41, reading "5 (2-n-" should read -- 5-(2-n- --.
Column 11, line 4, reading "centyl" should read -- pentyl --.
Column 12, line 68, reading "8 20" should read -- 8.20 --.
Column 13, line 3, reading "5" should read -- 5- --.
Column 14, lines 33-34, reading "3 oxathiolane 2,2-" should read
-- 3-oxathiolane-2,2- --.
Column 14, line 53, reading "12 48" should read -- 12.48 --.
Column 15, line 40, reading "2,4 dihydroxy-" should read -- 2,4-dihydroxy- --.
Column 15, line 44, reading "tetra n-" should read -- tetra-n- --.
Column 16, line 8, reading "3 oxathiolane-" should read -- 3-oxathiolane- --.
Column 16, lines 38-39, reading "8 tetrahydro naphthalene-" should read
--8-tetrahydronaphthalene- --.
Column 16, line 41, reading "tetra n-" should read -- tetra-n- --.
Column 17, line 38, reading "2 n propylphenol" should read
-- 2-n-propylphenol --.

UNITED STATES PATENT AND TRADEMARK OFFICE
CERTIFICATE OF CORRECTION

PATENT NO. : 4,923,891

DATED : May 8, 1990

INVENTOR(S) : Deason, et al.

It is certified that error appears in the above-identified patent and that said Letters Patent is hereby corrected as shown below:

Column 17, lines 41-42, reading "tetra n butylammonium" should read
-- tetra-n-butylammonium --.
Column 17, lines 50-51, reading "-oxathiolane 2,2-" should read
-- -oxathiolane-2,2- --.
Column 19, lines 48-49, reading "tetra n-" should read -- tetra-n- --.
Column 21, line 66, reading "$C_{26}H_{38}O_7S_3$.2HOAc" should read
-- $C_{26}H_{38}O_7S_3$·2HOAc --. This error regarding the misplacement of the dot (·) occurs in various circumstances throughout the remainder of the patent.
Column 23, line 10, reading "54 64" should read -- 54.64 --.
Column 27, line 61, reading "m chloroperbenzoic" should read
-- m-chloroperbenzoic --.
Column 28, line 60, reading "3 (2-" should read -- 3-(2- --.
Column 29, line 38, reading "7 29; S, 18 98." should read -- 7.29; S, 18.98 --.
Column 32, line 27, reading "52 53" should read -- 52.53 --.
Column 37, line 35, reading "-acetylphenoxy) 1-" should read
-- -acetylphenoxy)-1- --.
Column 38, line 42, "$C_{23}H_{34}O_6S_3$ $CH_3CO_2H$" should read
-- $C_{23}H_{34}O_6S_3$·$CH_3CO_2H$ --.
Column 40, line 63, reading "1 06 g" should read -- 1.06 g --.
Column 40, line 66, reading "$C_{21}H_{30}O_5S_3$ 0.33 EtOAc" should read
-- $C_{21}H_{30}O_5S_3$·0.33 EtOAc --.
Column 42, line 28, reading "acetylphenoxy) 1-bromopropane" should read
-- acetylphenoxy)-1-bromopropane --.
Column 45, the fourth structure, that portion of the structure reading should read 

Column 45, the fifth structure, that portion of the structure reading

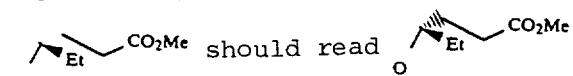 should read 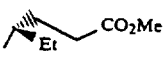

UNITED STATES PATENT AND TRADEMARK OFFICE
CERTIFICATE OF CORRECTION

PATENT NO. : 4,923,891

DATED : May 8, 1990

INVENTOR(S) : Deason, et al.

It is certified that error appears in the above-identified patent and that said Letters Patent is hereby corrected as shown below:

Column 48, line 53, reading "-(4-acetyl-" should read -- 3-(4-acetyl- --.
Column 48, line 58, reading "-(4-acetyl-" should read -- 3-(4-acetyl- --.
Column 48, line 68, reading "thiol" should read -- thio] --.
Column 49, line 30, reading "$C_{24}H_{36}O_6S_2C$," should read -- $C_{24}H_{36}O_6S_2$: C, --.
Column 50, line 11, reading "ppm" should read -- (ppm --.

Column 53, line 36, reading "(PPm)" should read -- (ppm) --.
Column 54, the first structure, that portion of the structure reading [structure] should read [structure]
Column 54, the second structure, that portion of the structure reading [structure] should read [structure]
Column 55, the first structure, that portion of the structure reading [structure] should read [structure]
Column 55, the second structure, that portion of the structure reading [structure] should read [structure]
Column 56, line 4, reading "Anal. Calcd. for C," should read -- Anal. Calcd. for $C_{23}H_{34}O_6S_2$: C, --.
Column 56, line 32, reading "Synthesis" should read -- (b) Synthesis --.
Column 59, line 20, reading "claim 4" should read -- claim 1 --.
Col. 59, lines 29-30, reading "4-[[[3-(acetyl-" should read --4-[[[3-(4-acetyl- --.
Col. 59, line 42, read "-(4-acetyl-" should read --3-(4-acetyl- --.
Column 59, line 51, reading "ethyl" should read -- methyl --.
Col. 59, line 63, reading "-2methyl-" should read -- -2-methyl- --.

UNITED STATES PATENT AND TRADEMARK OFFICE
CERTIFICATE OF CORRECTION

PATENT NO. : 4,923,891

DATED : May 8, 1990

INVENTOR(S) : Deason, et al.

It is certified that error appears in the above-identified patent and that said Letters Patent is hereby corrected as shown below:

Column 59, lines 66-67, reading "-propylphenoxypropyl]thio]methyl-2-methyl-1,3-dithiolane-2-butanoic acid" should read -- -propylphenoxy)propyl]thio]-methyl]-2-ethyl-1,3-oxathiolane-2-propanoic acid --.
Column 60, line 3, reading "-thio" should read -- thio --.
Column 61, line 57, reading "-propylphenoxy]thio]" should read
-- -propylphenoxy)propyl]thio] --.
Column 61, line 61, reading "thio methyl" should read -- thio]methyl --.
Column 61, line 65, reading "thio methyl" should read -- thio]methyl --.

Column 53, lines 4-6, reading "chromatographed on silica gel (Waters PrepPak concentrated in vacuo. The residual oil was 500/Silica)" should read -- concentrated in vacuo. The residual oil was chromatographed on silica gel (Waters PrepPak-500/Silica) --.

Signed and Sealed this

Twenty-second Day of December, 1992

Attest:

DOUGLAS B. COMER

*Attesting Officer*  *Acting Commissioner of Patents and Trademarks*